US012496081B2

(12) United States Patent
Dederich et al.

(10) Patent No.: US 12,496,081 B2
(45) Date of Patent: Dec. 16, 2025

(54) CATHETER FOR USE WITH CLOT TREATMENT SYSTEMS

(71) Applicant: Inari Medical, Inc., Irvine, CA (US)

(72) Inventors: Aaron Dederich, San Clemente, CA (US); Jakub Marek Truty, Anaheim, CA (US); Brian Edward Merritt, San Clemente, CA (US); Thien Mai, Santa Ana, CA (US)

(73) Assignee: Inari Medical, Inc., Irvine, CA (US)

( * ) Notice: Subject to any disclaimer, the term of this patent is extended or adjusted under 35 U.S.C. 154(b) by 192 days.

(21) Appl. No.: 18/408,177

(22) Filed: Jan. 9, 2024

(65) Prior Publication Data

US 2024/0225674 A1 Jul. 11, 2024

Related U.S. Application Data

(60) Provisional application No. 63/437,885, filed on Jan. 9, 2023.

(51) Int. Cl.

*A61B 17/221* (2006.01)
*A61B 17/00* (2006.01)
*A61B 17/22* (2006.01)

(52) U.S. Cl.

CPC .. *A61B 17/221* (2013.01); *A61B 2017/00336* (2013.01); *A61B 2017/00367* (2013.01);

(Continued)

(58) Field of Classification Search

CPC ............ A61B 17/22031; A61B 17/221; A61B 2017/00336; A61B 2017/00367;

(Continued)

(56) References Cited

U.S. PATENT DOCUMENTS 1,101,890 A 6/1914 Tunstead
2,502,639 A 4/1950 Blake (Continued)

FOREIGN PATENT DOCUMENTS

AU 2015210338 8/2015
CN 102186427 9/2011

(Continued)

OTHER PUBLICATIONS

US 12,114,876 B2, 10/2024, Quick et al. (withdrawn)

(Continued)

*Primary Examiner* — Kankindi Rwego
(74) *Attorney, Agent, or Firm* — Perkins Coie LLP

(57) ABSTRACT

Disclosed herein are catheters for use with clot treatment systems, and associated devices and methods. The catheter can include an outer sheath, an outer sheath drive component operably coupled to the outer sheath, a guidewire sheath slidably disposed within the outer sheath, a guidewire sheath drive component operably coupled to the guidewire sheath and slidably disposed within the outer sheath drive component, and a clot treatment component. During a clot treatment procedure, the outer sheath drive component can be moved proximally and/or the guidewire sheath drive component can be moved distally to cause corresponding movement of the outer sheath and/or guidewire sheath, respectively, and transition the catheter between a first configuration, in which the clot treatment component can be positioned within the outer sheath, and a second configuration, in which at least part of the clot treatment component can extend beyond the outer sheath.

32 Claims, 10 Drawing Sheets

(52) U.S. Cl.
CPC ............... *A61B 2017/00982* (2013.01); *A61B 2017/22038* (2013.01); *A61B 2017/2215* (2013.01)

(58) Field of Classification Search
CPC ........... A61B 2017/00982; A61B 2017/22034; A61B 2017/22035; A61B 2017/22038; A61B 2017/2212; A61B 2017/2215; A61B 2017/2217; A61M 25/01; A61M 25/0169; A61M 25/0172; A61M 2025/0681; A61M 2025/0175; A61M 2025/0183
USPC ......................................... 606/127, 159, 200
See application file for complete search history.

(56) References Cited

U.S. PATENT DOCUMENTS 2,707,954 A 5/1955 J. L., Sr.
2,784,717 A 3/1957 Thompson
2,846,179 A 8/1958 Monckton
2,955,592 A 10/1960 Maclean
3,088,363 A 5/1963 Sparks
3,197,173 A 7/1965 Taubenheim
3,383,131 A 5/1968 Rosfelder
3,416,531 A 12/1968 Edwards
3,435,826 A 4/1969 Fogarty
3,438,607 A 4/1969 Williams et al.
3,515,137 A 6/1970 Santomieri
3,661,144 A 5/1972 Jensen et al.
3,675,657 A 7/1972 Gauthier
3,785,380 A 1/1974 Brumfield
3,860,006 A 1/1975 Patel
3,863,624 A 2/1975 Gram
3,892,161 A 7/1975 Sokol
3,923,065 A 12/1975 Nozick et al.
4,030,503 A 6/1977 Clark, III
4,034,642 A 7/1977 Iannucci et al.
4,036,232 A 7/1977 Genese
4,187,849 A 2/1980 Stim
4,222,380 A 9/1980 Terayama
4,243,040 A 1/1981 Beecher
4,287,808 A 9/1981 Leonard et al.
4,324,262 A 4/1982 Hall
4,393,872 A 7/1983 Reznik et al.
4,401,107 A 8/1983 Harber et al.
4,469,100 A 9/1984 Hardwick
4,523,738 A 6/1985 Raftis et al.
4,551,862 A 11/1985 Haber
4,604,094 A 8/1986 Shook
4,611,594 A 9/1986 Grayhack et al.
4,634,421 A 1/1987 Hegemann
4,643,184 A 2/1987 Mobin-Uddin
4,646,736 A 3/1987 Auth et al.
4,650,466 A 3/1987 Luther
4,693,257 A 9/1987 Markham
4,705,518 A 11/1987 Baker et al.
4,776,337 A 10/1988 Palmaz
4,790,812 A 12/1988 Hawkins, Jr. et al.
4,826,483 A 5/1989 Molnar, IV
4,863,440 A 9/1989 Chin et al.
4,870,953 A 10/1989 DonMichael et al.
4,880,408 A 11/1989 Cumes et al.
4,883,458 A 11/1989 Shiber
4,886,062 A 12/1989 Wiktor
4,890,611 A 1/1990 Monfort et al.
4,898,575 A 2/1990 Fischell et al.
4,946,440 A 8/1990 Hall
4,960,259 A 10/1990 Sunnanvader et al.
4,978,341 A 12/1990 Niederhauser
4,981,478 A 1/1991 Evard et al.
5,030,201 A 7/1991 Palestrant
5,053,008 A 10/1991 Bajaj
5,059,178 A 10/1991 Ya
5,100,423 A 3/1992 Fearnot
5,127,626 A 7/1992 Hilal et al.
5,129,910 A 7/1992 Phan et al.
5,135,484 A 8/1992 Wright
5,154,724 A 10/1992 Andrews
5,156,594 A * 10/1992 Keith ................. A61M 25/104
604/528
5,158,533 A 10/1992 Strauss et al.
5,158,564 A 10/1992 Schnepp-Pesch et al.
5,192,274 A 3/1993 Bierman
5,192,286 A 3/1993 Phan et al.
5,192,290 A 3/1993 Hilal
5,197,485 A 3/1993 Grooters
5,234,403 A 8/1993 Yoda et al.
5,242,461 A 9/1993 Kortenbach et al.
5,244,619 A 9/1993 Burnham
5,246,011 A 9/1993 Caillouette
5,323,514 A 6/1994 Masuda et al.
5,329,923 A 7/1994 Lundquist
5,360,417 A 11/1994 Gravener et al.
5,364,345 A 11/1994 Lowery et al.
5,376,071 A 12/1994 Henderson
5,376,101 A 12/1994 Green et al.
5,383,887 A 1/1995 Nadal
5,389,100 A 2/1995 Bacich et al.
5,391,152 A 2/1995 Patterson et al.
5,419,774 A 5/1995 Willard et al.
5,421,824 A 6/1995 Clement et al.
5,429,610 A 7/1995 Vaillancourt
5,443,443 A 8/1995 Shiber
5,456,667 A 10/1995 Ham et al.
5,476,450 A 12/1995 Ruggio
5,484,418 A 1/1996 Quiachon et al.
5,490,859 A 2/1996 Mische et al.
5,496,365 A 3/1996 Sgro
5,527,326 A 6/1996 Hermann et al.
5,549,626 A 8/1996 Miller et al.
5,591,137 A 1/1997 Stevens
5,639,276 A 6/1997 Weinstock et al.
5,653,684 A 8/1997 Laptewicz et al.
5,662,703 A 9/1997 Yurek et al.
5,746,758 A 5/1998 Nordgren et al.
5,749,858 A 5/1998 Cramer
5,769,816 A 6/1998 Barbut et al.
5,782,817 A 7/1998 Franzel et al.
5,800,457 A 9/1998 Gelbfish
5,827,229 A 10/1998 Auth et al.
5,846,251 A 12/1998 Hart
5,860,938 A 1/1999 Lafontaine et al.
5,867,385 A 2/1999 Ikari et al.
5,873,866 A 2/1999 Kondo et al.
5,873,882 A 2/1999 Straub et al.
5,876,414 A 3/1999 Straub
5,895,406 A 4/1999 Gray et al.
5,908,435 A 6/1999 Samuels
5,911,710 A 6/1999 Barry et al.
5,911,728 A 6/1999 Sepetka et al.
5,911,733 A 6/1999 Parodi
5,911,754 A 6/1999 Kanesaka et al.
5,941,869 A 8/1999 Patterson et al.
5,947,985 A 9/1999 Imram
5,951,539 A 9/1999 Nita et al.
5,954,737 A 9/1999 Lee
5,971,938 A 10/1999 Hart et al.
5,971,958 A 10/1999 Zhang
5,972,019 A 10/1999 Engelson et al.
5,974,938 A 11/1999 Lloyd
5,989,233 A 11/1999 Yoon
5,993,483 A 11/1999 Gianott
6,017,335 A 1/2000 Burnham
6,030,397 A 2/2000 Moneti et al.
6,059,745 A 5/2000 Gelbfish
6,059,814 A 5/2000 Ladd
6,066,158 A 5/2000 Engelson et al.
6,068,645 A 5/2000 Tu
6,126,635 A 10/2000 Simpson et al.
6,142,987 A 11/2000 Tsugita
6,146,396 A 11/2000 Konya et al.
6,146,403 A 11/2000 St. Germain
6,152,144 A 11/2000 Lesh et al.
6,152,909 A 11/2000 Bagaoisan et al.

(56) References Cited

U.S. PATENT DOCUMENTS 6,152,946 A 11/2000 Broome et al.
6,156,055 A 12/2000 Ravenscroft
6,159,230 A 12/2000 Samuels
6,165,196 A 12/2000 Stack et al.
6,168,579 B1 1/2001 Tsugita
6,179,859 B1 1/2001 Bates et al.
6,221,006 B1 4/2001 Dubrul et al.
6,228,060 B1 5/2001 Howell
6,238,412 B1 5/2001 Dubrul et al.
6,245,078 B1 6/2001 Ouchi
6,245,089 B1 6/2001 Daniel et al.
6,254,571 B1 7/2001 Hart
6,258,115 B1 7/2001 Dubrul
6,264,663 B1 7/2001 Cano
6,306,163 B1 10/2001 Fitz
6,322,572 B1 11/2001 Lee
6,350,271 B1 2/2002 Kurz et al.
6,361,545 B1 3/2002 Macoviak et al.
6,364,895 B1 4/2002 Greenhalgh
6,368,339 B1 4/2002 Amplatz
6,383,205 B1 5/2002 Samson et al.
6,402,771 B1 6/2002 Palmer et al.
6,413,235 B1 7/2002 Parodi
6,423,032 B2 7/2002 Parodi
6,432,122 B1 8/2002 Gilson et al.
6,436,085 B1 8/2002 Lauer
6,451,036 B1 9/2002 Heitzmann et al.
6,458,103 B1 10/2002 Albert et al.
6,475,236 B1 11/2002 Roubin et al.
6,485,502 B2 11/2002 Don Michael
6,508,782 B1 1/2003 Evans et al.
6,511,492 B1 1/2003 Rosenbluth et al.
6,514,273 B1 2/2003 Voss et al.
6,530,923 B1 3/2003 Dubrul et al.
6,530,935 B2 3/2003 Wensel et al.
6,540,722 B1 4/2003 Boyle et al.
6,544,276 B1 4/2003 Azizi
6,544,278 B1 4/2003 Vrba et al.
6,544,279 B1 4/2003 Hopkins et al.
6,551,342 B1 4/2003 Shen et al.
6,564,828 B1 5/2003 Ishida
6,569,181 B1 5/2003 Burns
6,575,995 B1 6/2003 Huter et al.
6,589,263 B1 7/2003 Hopkins et al.
6,589,264 B1 7/2003 Barbut et al.
6,596,011 B2 7/2003 Johnson et al.
6,602,271 B2 8/2003 Adams et al.
6,605,074 B2 8/2003 Zadno-azizi et al.
6,605,102 B1 8/2003 Mazzocchi et al.
6,610,077 B1 8/2003 Hancock et al.
6,620,148 B1 9/2003 Tsugita
6,620,179 B2 9/2003 Brook et al.
6,620,182 B1 9/2003 Khosravi et al.
6,623,460 B1 9/2003 Heck
6,635,068 B1 10/2003 Dubrul et al.
6,645,222 B1 11/2003 Parodi et al.
6,660,013 B2 12/2003 Rabiner et al.
6,660,014 B2 12/2003 Demarais et al.
6,663,650 B2 12/2003 Sepetka et al.
6,692,504 B2 2/2004 Kurz et al.
6,699,260 B2 3/2004 Dubrul
6,702,830 B1 3/2004 Demarais et al.
6,719,717 B1 4/2004 Johnson et al.
6,755,847 B2 6/2004 Eskuri
6,767,353 B1 7/2004 Shiber
6,790,204 B2 9/2004 Zadno-azizi et al.
6,800,080 B1 10/2004 Bates
6,818,006 B2 11/2004 Douk et al.
6,824,545 B2 11/2004 Sepetka et al.
6,824,550 B1 11/2004 Noriega et al.
6,824,553 B1 11/2004 Gene et al.
6,830,561 B2 12/2004 Jansen et al.
6,846,029 B1 1/2005 Ragner et al.
6,902,540 B2 6/2005 Dorros et al.
6,908,455 B2 6/2005 Hajianpour
6,939,361 B1 9/2005 Kleshinski
6,942,682 B2 9/2005 Vrba et al.
6,945,977 B2 9/2005 Demarais et al.
6,960,189 B2 11/2005 Bates et al.
6,960,222 B2 11/2005 Vo et al.
7,004,931 B2 2/2006 Hogendijk
7,004,954 B1 2/2006 Voss et al.
7,036,707 B2 5/2006 Aota et al.
7,041,084 B2 5/2006 Fotjik
7,052,500 B2 5/2006 Bashiri et al.
7,056,328 B2 6/2006 Arnott
7,063,707 B2 6/2006 Bose et al.
7,069,835 B2 7/2006 Nishri et al.
7,094,249 B1 8/2006 Thomas et al.
7,122,034 B2 10/2006 Belhe et al.
7,128,073 B1 10/2006 van der Burg et al.
7,152,605 B2 12/2006 Khairkhahan et al.
7,179,273 B1 2/2007 Palmer et al.
7,223,253 B2 5/2007 Hogendijk
7,232,432 B2 6/2007 Fulton, III et al.
7,244,243 B2 7/2007 Lary
7,285,126 B2 10/2007 Sepetka et al.
7,300,458 B2 11/2007 Henkes et al.
7,306,618 B2 12/2007 Demond et al.
7,320,698 B2 1/2008 Eskuri
7,323,002 B2 1/2008 Johnson et al.
7,331,980 B2 2/2008 Dubrul et al.
7,481,805 B2 1/2009 Magnusson
7,534,234 B2 5/2009 Fotjik
7,578,830 B2 8/2009 Kusleika et al.
7,621,870 B2 11/2009 Berrada et al.
7,674,247 B2 3/2010 Fotjik
7,678,131 B2 3/2010 Muller
7,691,121 B2 4/2010 Rosenbluth et al.
7,695,458 B2 4/2010 Belley et al.
7,713,282 B2 5/2010 Frazier et al.
7,722,641 B2 5/2010 van der Burg et al.
7,763,010 B2 7/2010 Evans et al.
7,766,934 B2 8/2010 Pal et al.
7,775,501 B2 8/2010 Kees
7,780,696 B2 8/2010 Daniel et al.
7,815,608 B2 10/2010 Schafersman et al.
7,905,877 B1 3/2011 Oscar et al.
7,905,896 B2 3/2011 Straub
7,938,809 B2 5/2011 Lampropoulos et al.
7,938,820 B2 5/2011 Webster et al.
7,967,790 B2 6/2011 Whiting et al.
7,976,511 B2 7/2011 Fotjik
7,993,302 B2 8/2011 Hebert et al.
7,993,363 B2 8/2011 Demond et al.
8,021,351 B2 9/2011 Boldenow et al.
8,043,313 B2 10/2011 Krolik et al.
8,052,640 B2 11/2011 Fiorella et al.
8,057,496 B2 11/2011 Fischer, Jr.
8,057,497 B1 11/2011 Raju et al.
8,066,757 B2 11/2011 Ferrera et al.
8,070,694 B2 12/2011 Galdonik et al.
8,070,769 B2 12/2011 Broome
8,070,791 B2 12/2011 Ferrera et al.
8,075,510 B2 12/2011 Aklog et al.
8,080,032 B2 12/2011 van der Burg et al.
8,088,140 B2 1/2012 Ferrera et al.
8,092,486 B2 1/2012 Berrada et al.
8,100,935 B2 1/2012 Rosenbluth et al.
8,109,962 B2 2/2012 Pal
8,118,275 B2 2/2012 Mialhe
8,118,829 B2 2/2012 Carrison et al.
8,187,465 B2 5/2012 Nierich
8,197,493 B2 6/2012 Ferrera et al.
8,246,641 B2 8/2012 Osborne et al.
8,261,648 B1 9/2012 Marchand et al.
8,267,897 B2 9/2012 Wells
8,298,257 B2 10/2012 Sepetka et al.
8,317,748 B2 11/2012 Fiorella et al.
8,337,450 B2 12/2012 Fotjik
RE43,902 E 1/2013 Hopkins et al.
8,343,167 B2 1/2013 Henson
8,357,178 B2 1/2013 Grandfield et al.
8,361,104 B2 1/2013 Jones et al.

(56) References Cited

U.S. PATENT DOCUMENTS 8,409,215 B2 4/2013 Sepetka et al.
8,439,858 B2 5/2013 Huang et al.
8,480,708 B2 7/2013 Kassab et al.
8,486,105 B2 7/2013 Demond et al.
8,491,539 B2 7/2013 Fotjik
8,512,352 B2 8/2013 Martin
8,523,897 B2 9/2013 van der Burg et al.
8,529,596 B2 9/2013 Grandfield et al.
8,535,283 B2 9/2013 Heaton et al.
8,535,334 B2 9/2013 Martin
8,535,343 B2 9/2013 van der Burg et al.
8,545,526 B2 10/2013 Martin et al.
8,568,432 B2 10/2013 Straub
8,568,465 B2 10/2013 Freudenthal et al.
8,574,262 B2 11/2013 Ferrera et al.
8,579,915 B2 11/2013 French et al.
8,585,713 B2 11/2013 Ferrera et al.
8,608,754 B2 12/2013 Wensel et al.
8,613,717 B2 12/2013 Aklog et al.
8,632,584 B2 1/2014 Henkes et al.
8,647,367 B2 2/2014 Kassab et al.
8,657,867 B2 2/2014 Dorn et al.
8,696,622 B2 4/2014 Fiorella et al.
8,715,314 B1 5/2014 Janardhan et al.
8,721,714 B2 5/2014 Kelley
8,753,322 B2 6/2014 Hu et al.
8,764,730 B2 7/2014 Taber
8,771,289 B2 7/2014 Mohiuddin et al.
8,777,893 B2 7/2014 Malewicz
8,784,441 B2 7/2014 Rosenbluth et al.
8,784,442 B2 7/2014 Jones et al.
8,784,469 B2 7/2014 Kassab
8,795,305 B2 8/2014 Martin et al.
8,795,317 B2 8/2014 Grandfield et al.
8,795,345 B2 8/2014 Grandfield et al.
8,801,748 B2 8/2014 Martin
8,808,259 B2 8/2014 Walton et al.
8,814,927 B2 8/2014 Shin et al.
8,820,207 B2 9/2014 Marchand et al.
8,826,791 B2 9/2014 Thompson et al.
8,828,044 B2 9/2014 Aggerholm et al.
8,833,224 B2 9/2014 Thompson et al.
8,834,519 B2 9/2014 van der Burg et al.
8,845,621 B2 9/2014 Fotjik
8,852,205 B2 10/2014 Brady et al.
8,852,226 B2 10/2014 Gilson et al.
8,939,991 B2 1/2015 Krolik et al.
8,945,143 B2 2/2015 Ferrera et al.
8,945,172 B2 2/2015 Ferrera et al.
8,956,384 B2 2/2015 Berrada et al.
8,992,504 B2 3/2015 Castella et al.
9,005,172 B2 4/2015 Chung
9,011,551 B2 4/2015 Oral et al.
9,028,401 B1 5/2015 Bacich et al.
9,044,575 B2 6/2015 Beasley et al.
9,072,537 B2 7/2015 Grandfield et al.
9,078,682 B2 7/2015 Lenker et al.
9,101,382 B2 8/2015 Krolik et al.
9,125,683 B2 9/2015 Farhangnia et al.
9,126,016 B2 9/2015 Fulton
9,126,020 B2 9/2015 Farhangnia et al.
9,149,609 B2 10/2015 Ansel et al.
9,155,552 B2 10/2015 Ulm, III
9,161,766 B2 10/2015 Slee et al.
9,168,043 B2 10/2015 van der Burg et al.
9,173,668 B2 11/2015 Ulm, III
9,186,487 B2 11/2015 Dubrul et al.
D744,639 S 12/2015 Aklog et al.
9,204,887 B2 12/2015 Cully et al.
9,216,277 B2 12/2015 Myers
9,241,669 B2 1/2016 Pugh et al.
9,254,352 B2 2/2016 Kumar et al.
9,259,237 B2 2/2016 Quick et al.
9,265,512 B2 2/2016 Carrison et al.
9,283,066 B2 3/2016 Hopkins et al.
9,301,769 B2 4/2016 Brady et al.
9,351,747 B2 5/2016 Kugler et al.
9,358,037 B2 6/2016 Farhangnia et al.
9,402,938 B2 8/2016 Aklog et al.
9,439,664 B2 9/2016 Sos
9,439,751 B2 9/2016 White et al.
9,456,834 B2 10/2016 Folk
9,463,035 B1 10/2016 Greenhalgh et al.
9,463,036 B2 10/2016 Brady et al.
9,492,635 B2 11/2016 Beasley et al.
9,526,864 B2 12/2016 Quick
9,526,865 B2 12/2016 Quick
9,532,792 B2 1/2017 Galdonik et al.
9,545,464 B2 1/2017 Roche et al.
9,566,073 B2 2/2017 Kassab et al.
9,566,179 B2 2/2017 Andreas et al.
9,566,424 B2 2/2017 Pessin
9,579,116 B1 2/2017 Nguyen et al.
9,581,942 B1 2/2017 Shippert
9,616,213 B2 4/2017 Furnish et al.
9,636,206 B2 5/2017 Nguyen et al.
9,643,035 B2 5/2017 Mastenbroek
9,662,129 B2 5/2017 Galdonik et al.
9,700,332 B2 7/2017 Marchand et al.
9,717,488 B2 8/2017 Kassab et al.
9,717,514 B2 8/2017 Martin et al.
9,717,519 B2 8/2017 Rosenbluth et al.
9,744,024 B2 8/2017 Nguyen et al.
9,757,137 B2 9/2017 Krolik et al.
9,827,084 B2 11/2017 Bonnette et al.
9,827,364 B2 11/2017 Peticca et al.
9,844,386 B2 12/2017 Nguyen et al.
9,844,387 B2 12/2017 Marchand et al.
9,844,643 B2 12/2017 Beasley et al.
9,848,975 B2 12/2017 Hauser
9,849,014 B2 12/2017 Kusleika
9,884,387 B2 2/2018 Plha
9,937,321 B2 4/2018 Welch et al.
9,962,178 B2 5/2018 Greenhalgh et al.
9,980,813 B2 5/2018 Eller
9,999,493 B2 6/2018 Nguyen et al.
10,004,531 B2 6/2018 Rosenbluth et al.
10,010,335 B2 7/2018 Greenhalgh et al.
10,016,206 B1 7/2018 Yang
10,016,266 B2 7/2018 Hauser
10,028,759 B2 7/2018 Wallace et al.
10,045,790 B2 8/2018 Cox et al.
10,058,339 B2 8/2018 Galdonik et al.
10,098,651 B2 10/2018 Marchand et al.
10,130,385 B2 11/2018 Farhangnia et al.
10,130,795 B2 11/2018 Parhangnia et al.
10,179,224 B2 1/2019 Yang et al.
10,183,147 B2 1/2019 Yang et al.
10,183,159 B2 1/2019 Nobles et al.
10,188,829 B2 1/2019 Beasley et al.
10,195,320 B2 2/2019 Fisher et al.
10,226,263 B2 3/2019 Look et al.
10,238,406 B2 3/2019 Cox et al.
10,271,864 B2 4/2019 Greenhalgh et al.
10,327,883 B2 6/2019 Yachia
10,335,186 B2 7/2019 Rosenbluth et al.
10,342,571 B2 7/2019 Marchand et al.
10,349,960 B2 7/2019 Quick
10,383,644 B2 8/2019 Molaei et al.
10,383,983 B2 8/2019 Aklog et al.
10,384,034 B2 8/2019 Carrison et al.
10,426,510 B2 10/2019 Farhangnia et al.
10,426,644 B2 10/2019 Shrivastava et al.
10,441,745 B2 10/2019 Yang et al.
10,456,151 B2 10/2019 Slee et al.
10,456,555 B2 10/2019 Carrison et al.
10,471,234 B2 11/2019 Taber
10,478,535 B2 11/2019 Ogle
10,485,952 B2 11/2019 Carrison et al.
10,492,805 B2 12/2019 Culbert et al.
10,524,811 B2 1/2020 Marchand et al.
10,531,883 B1 1/2020 Deville et al.
10,537,710 B2 1/2020 Jalgaonkar et al.
10,561,440 B2 2/2020 Look et al.

(56) References Cited

U.S. PATENT DOCUMENTS

| | | | |
|---|---|---|---|
| 10,588,655 | B2 | 3/2020 | Rosenbluth et al. |
| 10,648,268 | B2 | 5/2020 | Jaffrey et al. |
| 10,661,053 | B2 | 5/2020 | Yang et al. |
| 10,695,159 | B2 | 6/2020 | Hauser |
| 10,709,471 | B2 | 7/2020 | Rosenbluth et al. |
| 10,729,455 | B2 | 8/2020 | Goyal et al. |
| 10,743,907 | B2 | 8/2020 | Bruzzi et al. |
| 10,772,636 | B2 | 9/2020 | Kassab et al. |
| 10,779,852 | B2 | 9/2020 | Bruzzi et al. |
| 10,779,855 | B2 | 9/2020 | Garrison |
| 10,799,331 | B2 | 10/2020 | Hauser |
| 10,799,671 | B2 | 10/2020 | Shimada et al. |
| 10,813,663 | B2 | 10/2020 | Bruzzi et al. |
| 10,828,061 | B2 | 11/2020 | Bonnette et al. |
| 10,835,711 | B2 | 11/2020 | Yang et al. |
| 10,874,421 | B2 | 12/2020 | Bruzzi et al. |
| 10,912,577 | B2 | 2/2021 | Marchand et al. |
| 10,926,060 | B2 | 2/2021 | Stern et al. |
| 10,939,932 | B1 | 3/2021 | Yang |
| 10,953,195 | B2 | 3/2021 | Jalgaonkar et al. |
| 10,960,114 | B2 | 3/2021 | Goisis |
| 10,967,111 | B2 | 4/2021 | Iida |
| 10,994,063 | B2 | 5/2021 | Fisher et al. |
| 11,000,682 | B2 | 5/2021 | Merritt et al. |
| 11,013,523 | B2 | 5/2021 | Arad Hadar |
| 11,058,445 | B2 | 7/2021 | Cox et al. |
| 11,058,451 | B2 | 7/2021 | Marchand et al. |
| 11,065,019 | B1 | 7/2021 | Chou et al. |
| 11,065,028 | B2 | 7/2021 | Parhangnia et al. |
| 11,147,571 | B2 | 10/2021 | Cox et al. |
| 11,147,948 | B2 | 10/2021 | Beasley et al. |
| 11,147,949 | B2 | 10/2021 | Yang et al. |
| 11,154,314 | B2 | 10/2021 | Quick |
| 11,166,703 | B2 | 11/2021 | Kassab et al. |
| 11,185,664 | B2 | 11/2021 | Carrison et al. |
| 11,197,684 | B1 | 12/2021 | Ngo et al. |
| 11,213,356 | B2 | 1/2022 | Tanner et al. |
| 11,224,450 | B2 | 1/2022 | Chou et al. |
| 11,224,721 | B2 | 1/2022 | Carrison et al. |
| 11,253,277 | B2 | 2/2022 | Buck et al. |
| 11,259,821 | B2 | 3/2022 | Buck et al. |
| 11,266,825 | B2 | 3/2022 | Peter et al. |
| 11,278,307 | B2 | 3/2022 | Bruzzi et al. |
| 11,305,094 | B2 | 4/2022 | Carrison et al. |
| 11,317,939 | B2 | 5/2022 | Bruzzi et al. |
| 11,337,714 | B2 | 5/2022 | Ferrera et al. |
| 11,383,064 | B2 | 7/2022 | Carrison et al. |
| 11,395,903 | B2 | 7/2022 | Carrison et al. |
| 11,406,418 | B2 | 8/2022 | Bruzzi et al. |
| 11,406,801 | B2 | 8/2022 | Fojtik et al. |
| 11,419,621 | B2 | 8/2022 | Goyal et al. |
| 11,433,218 | B2 | 9/2022 | Quick et al. |
| 11,439,799 | B2 | 9/2022 | Buck et al. |
| 11,457,936 | B2 | 10/2022 | Buck et al. |
| 11,478,262 | B2 | 10/2022 | Ngo et al. |
| 11,529,158 | B2 | 12/2022 | Hauser |
| 11,553,935 | B2 | 1/2023 | Buck et al. |
| 11,553,942 | B2 | 1/2023 | Bonnette et al. |
| 11,554,005 | B2 | 1/2023 | Merritt et al. |
| 11,559,382 | B2 | 1/2023 | Merritt et al. |
| 11,576,691 | B2 | 2/2023 | Chou et al. |
| 11,589,880 | B2 | 2/2023 | Aklog et al. |
| 11,596,768 | B2 | 3/2023 | Stern et al. |
| 11,607,483 | B2 | 3/2023 | Iida |
| 11,633,272 | B2 | 4/2023 | Buck et al. |
| 11,638,637 | B2 | 5/2023 | Buck et al. |
| 11,642,209 | B2 | 5/2023 | Merritt et al. |
| 11,648,028 | B2 | 5/2023 | Rosenbluth et al. |
| 11,672,561 | B2 | 6/2023 | Look et al. |
| 11,697,011 | B2 | 7/2023 | Merritt et al. |
| 11,697,012 | B2 | 7/2023 | Merritt et al. |
| 11,744,691 | B2 | 9/2023 | Merritt et al. |
| 11,806,033 | B2 | 11/2023 | Marchand et al. |
| 11,819,228 | B2 | 11/2023 | Buck et al. |
| 11,832,837 | B2 | 12/2023 | Hauser |
| 11,832,838 | B2 | 12/2023 | Hauser |
| 11,833,023 | B2 | 12/2023 | Hauser |
| 11,839,393 | B2 | 12/2023 | Hauser |
| 11,844,921 | B2 | 12/2023 | Merritt et al. |
| 11,849,963 | B2 | 12/2023 | Quick |
| 11,865,291 | B2 | 1/2024 | Merritt et al. |
| 11,890,180 | B2 | 2/2024 | Merritt et al. |
| 11,918,243 | B2 | 3/2024 | Marchand et al. |
| 11,918,244 | B2 | 3/2024 | Marchand et al. |
| 11,925,369 | B2 | 3/2024 | Hauser |
| 11,937,834 | B2 | 3/2024 | Dinh |
| 11,937,838 | B2 | 3/2024 | Cox et al. |
| 11,963,861 | B2 | 4/2024 | Strauss et al. |
| 11,969,178 | B2 | 4/2024 | Hauser |
| 11,969,331 | B2 | 4/2024 | Merritt et al. |
| 11,969,332 | B2 | 4/2024 | Merritt et al. |
| 11,969,333 | B2 | 4/2024 | Merritt et al. |
| 11,974,909 | B2 | 5/2024 | Merritt et al. |
| 11,974,910 | B2 | 5/2024 | Merritt et al. |
| 11,980,537 | B2 | 5/2024 | Merritt et al. |
| 11,986,382 | B2 | 5/2024 | Merritt et al. |
| 11,998,436 | B2 | 6/2024 | Merritt et al. |
| 12,016,580 | B2 | 6/2024 | Quick et al. |
| 12,023,057 | B2 | 7/2024 | Hauser |
| 12,102,343 | B2 | 10/2024 | Quick |
| 12,109,384 | B2 | 10/2024 | Merritt et al. |
| 2001/0004699 | A1 | 6/2001 | Gittings et al. |
| 2001/0031981 | A1 | 10/2001 | Evans et al. |
| 2001/0041881 | A1 | 11/2001 | Sarge et al. |
| 2001/0041909 | A1 | 11/2001 | Tsugita et al. |
| 2001/0049486 | A1 | 12/2001 | Evans et al. |
| 2001/0051810 | A1 | 12/2001 | Dubrul et al. |
| 2002/0022858 | A1 | 2/2002 | Demond et al. |
| 2002/0022859 | A1 | 2/2002 | Hogendijk |
| 2002/0026211 | A1 | 2/2002 | Khosravi et al. |
| 2002/0032455 | A1 | 3/2002 | Boock et al. |
| 2002/0049452 | A1 | 4/2002 | Kurz et al. |
| 2002/0095161 | A1 | 7/2002 | Dhindsa |
| 2002/0095171 | A1 | 7/2002 | Belef |
| 2002/0111648 | A1 | 8/2002 | Kusleika et al. |
| 2002/0120277 | A1 | 8/2002 | Hauschild et al. |
| 2002/0147458 | A1 | 10/2002 | Hiblar et al. |
| 2002/0151918 | A1 | 10/2002 | Lafontaine et al. |
| 2002/0156457 | A1 | 10/2002 | Fisher |
| 2002/0161392 | A1 | 10/2002 | Dubrul |
| 2002/0169474 | A1 | 11/2002 | Kusleika |
| 2002/0173819 | A1 | 11/2002 | Leeflang et al. |
| 2002/0188276 | A1 | 12/2002 | Evans et al. |
| 2003/0004536 | A1 | 1/2003 | Boylan et al. |
| 2003/0023263 | A1 | 1/2003 | Krolik et al. |
| 2003/0069601 | A1 | 4/2003 | Nowakowski et al. |
| 2003/0083693 | A1 | 5/2003 | Daniel et al. |
| 2003/0093106 | A1* | 5/2003 | Brady ........................... 606/200 |
| 2003/0100919 | A1 | 5/2003 | Hopkins et al. |
| 2003/0114875 | A1 | 6/2003 | Sjostrom |
| 2003/0116731 | A1 | 6/2003 | Hartley |
| 2003/0125663 | A1 | 7/2003 | Coleman et al. |
| 2003/0135151 | A1 | 7/2003 | Deng |
| 2003/0135230 | A1 | 7/2003 | Massey et al. |
| 2003/0135258 | A1 | 7/2003 | Andreas et al. |
| 2003/0153873 | A1 | 8/2003 | Luther et al. |
| 2003/0153973 | A1 | 8/2003 | Soun et al. |
| 2003/0168068 | A1 | 9/2003 | Poole et al. |
| 2003/0176884 | A1 | 9/2003 | Berrada et al. |
| 2003/0191425 | A1 | 10/2003 | Rosenblatt et al. |
| 2003/0191516 | A1 | 10/2003 | Weldon et al. |
| 2003/0208224 | A1 | 11/2003 | Broome |
| 2003/0216774 | A1 | 11/2003 | Larson |
| 2003/0225379 | A1 | 12/2003 | Schaffer et al. |
| 2004/0019310 | A1 | 1/2004 | Hogendijk |
| 2004/0039351 | A1 | 2/2004 | Barrett |
| 2004/0039412 | A1 | 2/2004 | Isshiki et al. |
| 2004/0068288 | A1 | 4/2004 | Palmer et al. |
| 2004/0073243 | A1 | 4/2004 | Sepetka et al. |
| 2004/0098033 | A1 | 5/2004 | Leeflang et al. |
| 2004/0102807 | A1 | 5/2004 | Kusleika et al. |
| 2004/0122359 | A1 | 6/2004 | Wenz et al. |
| 2004/0127936 | A1 | 7/2004 | Salahieh et al. |
| 2004/0133232 | A1 | 7/2004 | Rosenbluth et al. |

(56) References Cited

U.S. PATENT DOCUMENTS

2004/0138525 A1 7/2004 Saadat et al.
2004/0138692 A1 7/2004 Phung et al.
2004/0167567 A1 8/2004 Cano et al.
2004/0199201 A1 10/2004 Kellett et al.
2004/0199202 A1 10/2004 Dubrul et al.
2004/0260344 A1 12/2004 Lyons et al.
2004/0267272 A1 12/2004 Henniges et al.
2005/0004534 A1 1/2005 Lockwood et al.
2005/0033172 A1 2/2005 Dubrul et al.
2005/0038468 A1 2/2005 Panetta et al.
2005/0054995 A1 3/2005 Barzell et al.
2005/0055047 A1 3/2005 Greenhalgh
2005/0080398 A1 4/2005 Markel et al.
2005/0085769 A1 4/2005 MacMahon et al.
2005/0085826 A1 4/2005 Nair et al.
2005/0085846 A1 4/2005 Carrison et al.
2005/0085849 A1 4/2005 Sepetka et al.
2005/0119668 A1 6/2005 Teague et al.
2005/0131387 A1 6/2005 Pursley
2005/0177132 A1 8/2005 Lentz et al.
2005/0187570 A1 8/2005 Nguyen et al.
2005/0203605 A1 9/2005 Dolan
2005/0283165 A1 12/2005 Gadberry
2005/0283166 A1 12/2005 Greenhalgh et al.
2005/0283186 A1 12/2005 Berrada et al.
2006/0020286 A1 1/2006 Niermann
2006/0042786 A1 3/2006 West
2006/0047286 A1 3/2006 West
2006/0074401 A1 4/2006 Ross
2006/0079787 A1 4/2006 Whiting et al.
2006/0085952 A1 4/2006 Kaneko et al.
2006/0089533 A1 4/2006 Ziegler et al.
2006/0100662 A1 5/2006 Daniel et al.
2006/0149219 A1 7/2006 Calderon
2006/0155305 A1 7/2006 Freudenthal et al.
2006/0173525 A1 8/2006 Behl et al.
2006/0195137 A1 8/2006 Sepetka et al.
2006/0200221 A1 9/2006 Malewicz
2006/0217664 A1 9/2006 Hattler et al.
2006/0224177 A1 10/2006 Finitsis
2006/0229645 A1 10/2006 Bonnette et al.
2006/0247500 A1 11/2006 Voegele et al.
2006/0253145 A1 11/2006 Lucas
2006/0264905 A1 11/2006 Eskridge et al.
2006/0276874 A1 12/2006 Wilson et al.
2006/0282111 A1 12/2006 Morsi
2006/0293696 A1 12/2006 Fahey et al.
2007/0010787 A1 1/2007 Hackett et al.
2007/0038225 A1 2/2007 Osborne
2007/0093744 A1 4/2007 Elmaleh
2007/0112374 A1 5/2007 Paul, Jr. et al.
2007/0118165 A1 5/2007 DeMello et al.
2007/0149996 A1 6/2007 Coughlin
2007/0161963 A1 7/2007 Smalling
2007/0179513 A1 8/2007 Deutsch
2007/0191866 A1 8/2007 Palmer et al.
2007/0198028 A1 8/2007 Miloslavski et al.
2007/0208361 A1 9/2007 Okushi et al.
2007/0208367 A1 9/2007 Fiorella et al.
2007/0213753 A1 9/2007 Waller
2007/0213765 A1 9/2007 Adams et al.
2007/0233043 A1 10/2007 Dayton et al.
2007/0255252 A1 11/2007 Mehta
2007/0288054 A1 12/2007 Tanaka et al.
2008/0015541 A1 1/2008 Rosenbluth et al.
2008/0087853 A1 4/2008 Kees
2008/0088055 A1 4/2008 Ross
2008/0157017 A1 7/2008 Macatangay et al.
2008/0167678 A1 7/2008 Morsi
2008/0183136 A1 7/2008 Lenker et al.
2008/0228209 A1 9/2008 DeMello et al.
2008/0234715 A1 9/2008 Pesce et al.
2008/0234722 A1 9/2008 Bonnette et al.
2008/0262528 A1 10/2008 Martin
2008/0269798 A1 10/2008 Ramzipoor et al.
2008/0294096 A1 11/2008 Uber, III et al.
2008/0300466 A1 12/2008 Gresham
2008/0312681 A1 12/2008 Ansel et al.
2009/0018566 A1 1/2009 Escudero et al.
2009/0054918 A1 2/2009 Henson
2009/0062841 A1 3/2009 Amplatz et al.
2009/0069828 A1 3/2009 Martin et al.
2009/0076417 A1 3/2009 Jones
2009/0082857 A1 3/2009 Lashinski et al.
2009/0160112 A1 6/2009 Ostrovsky
2009/0163846 A1 6/2009 Aklog et al.
2009/0182362 A1 7/2009 Thompson et al.
2009/0192495 A1 7/2009 Ostrovsky et al.
2009/0281525 A1 11/2009 Harding et al.
2009/0292307 A1 11/2009 Razack
2009/0299393 A1 12/2009 Martin et al.
2009/0312786 A1 12/2009 Trask et al.
2010/0016837 A1 1/2010 Howat
2010/0030256 A1 2/2010 Dubrul et al.
2010/0042136 A1 2/2010 Berrada et al.
2010/0087844 A1 4/2010 Fischer, Jr.
2010/0087850 A1 4/2010 Razack
2010/0094201 A1 4/2010 Mallaby
2010/0106081 A1 4/2010 Brandeis
2010/0114017 A1 5/2010 Lenker et al.
2010/0114113 A1 5/2010 Dubrul et al.
2010/0121312 A1 5/2010 Gielenz et al.
2010/0137846 A1 6/2010 Desai et al.
2010/0190156 A1 7/2010 Van Wordragen et al.
2010/0204712 A1 8/2010 Mallaby
2010/0217276 A1 8/2010 Garrison et al.
2010/0249815 A1 9/2010 Jantzen et al.
2010/0268264 A1 10/2010 Bonnette et al.
2010/0318178 A1 12/2010 Rapaport et al.
2011/0009950 A1 1/2011 Grandfield et al.
2011/0034986 A1 2/2011 Chou et al.
2011/0034987 A1 2/2011 Kennedy
2011/0054405 A1 3/2011 Whiting et al.
2011/0060212 A1 3/2011 Slee et al.
2011/0071503 A1 3/2011 Takagi et al.
2011/0087173 A1 4/2011 Sibbitt, Jr. et al.
2011/0118817 A1 5/2011 Gunderson et al.
2011/0125181 A1 5/2011 Brady et al.
2011/0144592 A1 6/2011 Wong et al.
2011/0152823 A1 6/2011 Mohiuddin et al.
2011/0152889 A1 6/2011 Ashland
2011/0152993 A1 6/2011 Marchand et al.
2011/0160742 A1 6/2011 Ferrera et al.
2011/0160763 A1 6/2011 Ferrera et al.
2011/0190806 A1 8/2011 Wittens
2011/0196309 A1 8/2011 Wells
2011/0196414 A1 8/2011 Porter et al.
2011/0213290 A1 9/2011 Chin et al.
2011/0213403 A1 9/2011 Aboytes
2011/0224707 A1 9/2011 Miloslavski et al.
2011/0245807 A1 10/2011 Sakata et al.
2011/0251629 A1 10/2011 Galdonik et al.
2011/0264132 A1 10/2011 Strauss et al.
2011/0264133 A1 10/2011 Hanlon et al.
2011/0265681 A1 11/2011 Allen et al.
2011/0288529 A1 11/2011 Fulton
2011/0288572 A1 11/2011 Martin
2011/0309037 A1 12/2011 Lee
2011/0319917 A1 12/2011 Ferrera et al.
2012/0059309 A1 3/2012 di Palma et al.
2012/0059356 A1 3/2012 di Palma et al.
2012/0083824 A1 4/2012 Berrada et al.
2012/0083868 A1 4/2012 Shrivastava
2012/0089216 A1 4/2012 Rapaport et al.
2012/0095448 A1 4/2012 Kajii
2012/0101480 A1 4/2012 Ingle et al.
2012/0101510 A1 4/2012 Lenker et al.
2012/0109109 A1 5/2012 Kaji
2012/0138832 A1 6/2012 Townsend
2012/0143123 A1 6/2012 Agnew
2012/0143239 A1 6/2012 Aklog et al.
2012/0165919 A1 6/2012 Cox et al.
2012/0172918 A1 7/2012 Fifer et al.
2012/0179181 A1 7/2012 Straub et al.

(56) References Cited

U.S. PATENT DOCUMENTS

| | | | |
|---|---|---|---|
| 2012/0197277 | A1 | 8/2012 | Stinis |
| 2012/0232655 | A1 | 9/2012 | Lorrison et al. |
| 2012/0271105 | A1 | 10/2012 | Nakamura et al. |
| 2012/0271231 | A1 | 10/2012 | Agrawal |
| 2012/0277788 | A1 | 11/2012 | Cattaneo |
| 2012/0310166 | A1 | 12/2012 | Huff |
| 2013/0030460 | A1 | 1/2013 | Marks et al. |
| 2013/0035628 | A1 | 2/2013 | Garrison et al. |
| 2013/0046332 | A1 | 2/2013 | Jones et al. |
| 2013/0066348 | A1 | 3/2013 | Fiorella et al. |
| 2013/0092012 | A1 | 4/2013 | Marchand et al. |
| 2013/0096571 | A1 | 4/2013 | Massicotte et al. |
| 2013/0102996 | A1 | 4/2013 | Strauss |
| 2013/0116708 | A1 | 5/2013 | Ziniti et al. |
| 2013/0116721 | A1 | 5/2013 | Takagi et al. |
| 2013/0123705 | A1 | 5/2013 | Holm et al. |
| 2013/0126559 | A1 | 5/2013 | Cowan et al. |
| 2013/0144326 | A1 | 6/2013 | Brady et al. |
| 2013/0150793 | A1 | 6/2013 | Beissel et al. |
| 2013/0165871 | A1 | 6/2013 | Fiorella et al. |
| 2013/0184703 | A1 | 7/2013 | Shireman et al. |
| 2013/0190701 | A1 | 7/2013 | Kirn |
| 2013/0197454 | A1 | 8/2013 | Shibata et al. |
| 2013/0197567 | A1 | 8/2013 | Brady et al. |
| 2013/0204297 | A1 | 8/2013 | Melsheimer et al. |
| 2013/0226196 | A1 | 8/2013 | Smith |
| 2013/0270161 | A1 | 10/2013 | Kumar et al. |
| 2013/0281788 | A1 | 10/2013 | Garrison |
| 2013/0289608 | A1 | 10/2013 | Tanaka et al. |
| 2013/0317589 | A1 | 11/2013 | Martin et al. |
| 2013/0345739 | A1 | 12/2013 | Brady et al. |
| 2014/0005712 | A1 | 1/2014 | Martin |
| 2014/0005713 | A1 | 1/2014 | Bowman |
| 2014/0005715 | A1 | 1/2014 | Castella et al. |
| 2014/0005717 | A1 | 1/2014 | Martin et al. |
| 2014/0025048 | A1 | 1/2014 | Ward |
| 2014/0031856 | A1 | 1/2014 | Martin |
| 2014/0046133 | A1 | 2/2014 | Nakamura et al. |
| 2014/0046243 | A1 | 2/2014 | Ray et al. |
| 2014/0052161 | A1 | 2/2014 | Cully et al. |
| 2014/0074144 | A1 | 3/2014 | Shrivastava et al. |
| 2014/0121672 | A1 | 5/2014 | Folk |
| 2014/0155830 | A1 | 6/2014 | Bonnette et al. |
| 2014/0155908 | A1 | 6/2014 | Rosenbluth et al. |
| 2014/0155980 | A1 | 6/2014 | Turjman |
| 2014/0163615 | A1 | 6/2014 | Gadlage et al. |
| 2014/0180055 | A1 | 6/2014 | Glynn et al. |
| 2014/0180397 | A1 | 6/2014 | Gerberding et al. |
| 2014/0188127 | A1 | 7/2014 | Dubrul et al. |
| 2014/0188143 | A1 | 7/2014 | Martin et al. |
| 2014/0222070 | A1 | 8/2014 | Belson et al. |
| 2014/0236219 | A1 | 8/2014 | Dubrul et al. |
| 2014/0243882 | A1 | 8/2014 | Ma |
| 2014/0257253 | A1 | 9/2014 | Jemison |
| 2014/0257363 | A1 | 9/2014 | Lippert |
| 2014/0276403 | A1 | 9/2014 | Follmer et al. |
| 2014/0276592 | A1 | 9/2014 | Mottola et al. |
| 2014/0296868 | A1 | 10/2014 | Garrison et al. |
| 2014/0303658 | A1 | 10/2014 | Bonnette et al. |
| 2014/0318354 | A1 | 10/2014 | Thompson et al. |
| 2014/0324091 | A1 | 10/2014 | Rosenbluth et al. |
| 2014/0330286 | A1 | 11/2014 | Wallace et al. |
| 2014/0336691 | A1 | 11/2014 | Jones et al. |
| 2014/0343593 | A1 | 11/2014 | Chin et al. |
| 2014/0364896 | A1 | 12/2014 | Consigny |
| 2014/0371779 | A1 | 12/2014 | Vale et al. |
| 2015/0005781 | A1 | 1/2015 | Lund-Clausen et al. |
| 2015/0005792 | A1 | 1/2015 | Ahn |
| 2015/0018859 | A1 | 1/2015 | Quick et al. |
| 2015/0018860 | A1 | 1/2015 | Quick |
| 2015/0018929 | A1 | 1/2015 | Martin et al. |
| 2015/0025555 | A1 | 1/2015 | Sos |
| 2015/0032144 | A1 | 1/2015 | Holloway |
| 2015/0059908 | A1 | 3/2015 | Mollen |
| 2015/0088190 | A1 | 3/2015 | Jensen |
| 2015/0127035 | A1 | 5/2015 | Trapp et al. |
| 2015/0133990 | A1 | 5/2015 | Davidson |
| 2015/0150672 | A1 | 6/2015 | Ma |
| 2015/0164523 | A1 | 6/2015 | Brady et al. |
| 2015/0164666 | A1 | 6/2015 | Johnson et al. |
| 2015/0173782 | A1 | 6/2015 | Garrison et al. |
| 2015/0190155 | A1 | 7/2015 | Ulm, III |
| 2015/0190156 | A1 | 7/2015 | Ulm, III |
| 2015/0196380 | A1 | 7/2015 | Berrada et al. |
| 2015/0196744 | A1 | 7/2015 | Aboytes |
| 2015/0209058 | A1 | 7/2015 | Ferrera et al. |
| 2015/0209165 | A1 | 7/2015 | Grandfield et al. |
| 2015/0238207 | A1 | 8/2015 | Cox et al. |
| 2015/0250578 | A1 | 9/2015 | Cook et al. |
| 2015/0265299 | A1 | 9/2015 | Cooper et al. |
| 2015/0283309 | A1 | 10/2015 | Look et al. |
| 2015/0305756 | A1 | 10/2015 | Rosenbluth |
| 2015/0305859 | A1 | 10/2015 | Eller |
| 2015/0327875 | A1 | 11/2015 | Look et al. |
| 2015/0352325 | A1 | 12/2015 | Quick |
| 2015/0360001 | A1 | 12/2015 | Quick |
| 2015/0366690 | A1 | 12/2015 | Lumauig |
| 2015/0374391 | A1 | 12/2015 | Quick |
| 2016/0008014 | A1 | 1/2016 | Rosenbluth |
| 2016/0022293 | A1 | 1/2016 | Dubrul et al. |
| 2016/0030708 | A1 | 2/2016 | Casiello et al. |
| 2016/0038267 | A1 | 2/2016 | Allen et al. |
| 2016/0058540 | A1 | 3/2016 | Don Michael |
| 2016/0074627 | A1 | 3/2016 | Cottone |
| 2016/0106353 | A1 | 4/2016 | Schuetz et al. |
| 2016/0106448 | A1 | 4/2016 | Brady et al. |
| 2016/0106449 | A1 | 4/2016 | Brady et al. |
| 2016/0113663 | A1 | 4/2016 | Brady et al. |
| 2016/0113664 | A1 | 4/2016 | Brady et al. |
| 2016/0113665 | A1 | 4/2016 | Brady et al. |
| 2016/0113666 | A1 | 4/2016 | Quick |
| 2016/0128857 | A1 | 5/2016 | Kao |
| 2016/0135829 | A1 | 5/2016 | Holochwost et al. |
| 2016/0143721 | A1 | 5/2016 | Rosenbluth |
| 2016/0151605 | A1 | 6/2016 | Welch et al. |
| 2016/0192912 | A1 | 7/2016 | Kassab et al. |
| 2016/0206344 | A1 | 7/2016 | Bruzzi et al. |
| 2016/0220741 | A1 | 8/2016 | Garrison et al. |
| 2016/0220795 | A1 | 8/2016 | Korkuch et al. |
| 2016/0228134 | A1 | 8/2016 | Martin et al. |
| 2016/0262774 | A1 | 9/2016 | Honda |
| 2016/0262790 | A1 | 9/2016 | Rosenbluth et al. |
| 2016/0287276 | A1 | 10/2016 | Cox et al. |
| 2016/0367285 | A1 | 12/2016 | Sos |
| 2017/0014560 | A1 | 1/2017 | Minskoff et al. |
| 2017/0021130 | A1 | 1/2017 | Dye |
| 2017/0037548 | A1 | 2/2017 | Lee |
| 2017/0042571 | A1 | 2/2017 | Levi |
| 2017/0049942 | A1 | 2/2017 | Conlan et al. |
| 2017/0056032 | A1 | 3/2017 | Look et al. |
| 2017/0058623 | A1 | 3/2017 | Jaffrey et al. |
| 2017/0079672 | A1 | 3/2017 | Quick |
| 2017/0086864 | A1 | 3/2017 | Greenhalgh et al. |
| 2017/0100142 | A1 | 4/2017 | Look et al. |
| 2017/0105743 | A1 | 4/2017 | Vale et al. |
| 2017/0105745 | A1 | 4/2017 | Rosenbluth et al. |
| 2017/0112513 | A1 | 4/2017 | Marchand et al. |
| 2017/0112514 | A1 | 4/2017 | Marchand et al. |
| 2017/0113005 | A1 | 4/2017 | Linder et al. |
| 2017/0143359 | A1 | 5/2017 | Nguyen et al. |
| 2017/0143880 | A1 | 5/2017 | Luxon et al. |
| 2017/0143938 | A1 | 5/2017 | Ogle et al. |
| 2017/0172591 | A1 | 6/2017 | Ulm, III |
| 2017/0189041 | A1 | 7/2017 | Cox et al. |
| 2017/0196576 | A1 | 7/2017 | Long et al. |
| 2017/0233908 | A1 | 8/2017 | Kroczynski et al. |
| 2017/0238951 | A1 | 8/2017 | Yang et al. |
| 2017/0252057 | A1 | 9/2017 | Bonnette et al. |
| 2017/0265878 | A1 | 9/2017 | Marchand et al. |
| 2017/0281204 | A1 | 10/2017 | Garrison et al. |
| 2017/0303939 | A1 | 10/2017 | Greenhalgh et al. |
| 2017/0303942 | A1 | 10/2017 | Greenhalgh et al. |
| 2017/0303947 | A1 | 10/2017 | Greenhalgh et al. |
| 2017/0303948 | A1 | 10/2017 | Wallace et al. |

(56) References Cited

U.S. PATENT DOCUMENTS

2017/0319221 A1 11/2017 Chu
2017/0325839 A1 11/2017 Rosenbluth et al.
2017/0340867 A1 11/2017 Accisano, III
2017/0348014 A1 12/2017 Wallace et al.
2018/0014840 A1 1/2018 Panian
2018/0042623 A1 2/2018 Batiste
2018/0042624 A1 2/2018 Greenhalgh et al.
2018/0042626 A1 2/2018 Greenhalgh et al.
2018/0055999 A1 3/2018 Bare et al.
2018/0064453 A1 3/2018 Garrison et al.
2018/0064454 A1 3/2018 Losordo et al.
2018/0070968 A1 3/2018 Wallace et al.
2018/0078707 A1 3/2018 Loonan
2018/0092652 A1 4/2018 Marchand et al.
2018/0104404 A1 4/2018 Ngo-Chu
2018/0105963 A1 4/2018 Quick
2018/0125512 A1 5/2018 Nguyen et al.
2018/0184912 A1 7/2018 Al-Ali
2018/0193043 A1 7/2018 Marchand et al.
2018/0235742 A1 8/2018 Fields et al.
2018/0236205 A1 8/2018 Krautkremer et al.
2018/0250498 A1 9/2018 Stern et al.
2018/0256177 A1 9/2018 Cooper et al.
2018/0256178 A1 9/2018 Cox et al.
2018/0280623 A1 10/2018 Pilkington et al.
2018/0296240 A1 10/2018 Rosenbluth et al.
2018/0338770 A1 11/2018 Mogi et al.
2018/0339130 A1 11/2018 Ogle
2018/0344339 A1 12/2018 Cox et al.
2018/0361116 A1 12/2018 Quick et al.
2019/0000492 A1 1/2019 Casey et al.
2019/0015298 A1 1/2019 Beatty et al.
2019/0046219 A1 2/2019 Marchand et al.
2019/0070401 A1 3/2019 Merritt et al.
2019/0117244 A1 4/2019 Wallace et al.
2019/0133622 A1 5/2019 Wallace et al.
2019/0133623 A1 5/2019 Wallace et al.
2019/0133624 A1 5/2019 Wallace et al.
2019/0133625 A1 5/2019 Wallace et al.
2019/0133626 A1 5/2019 Wallace et al.
2019/0133627 A1 5/2019 Wallace et al.
2019/0150959 A1 5/2019 Cox et al.
2019/0216476 A1 7/2019 Barry et al.
2019/0223893 A1 7/2019 Gilvarry et al.
2019/0231373 A1 8/2019 Quick
2019/0239910 A1 8/2019 Brady et al.
2019/0321071 A1 10/2019 Marchand et al.
2019/0328411 A1 10/2019 Vale et al.
2019/0336142 A1 11/2019 Torrie et al.
2019/0336148 A1 11/2019 Greenhalgh et al.
2019/0365395 A1 12/2019 Tran et al.
2019/0366036 A1 12/2019 Jalgaonkar et al.
2019/0366049 A1 12/2019 Hannon et al.
2020/0022711 A1 1/2020 Look et al.
2020/0030579 A1 1/2020 Taber
2020/0046368 A1 2/2020 Merritt et al.
2020/0046940 A1 2/2020 Carrison et al.
2020/0054861 A1 2/2020 Korkuch et al.
2020/0069889 A1 3/2020 Lin
2020/0078029 A1 3/2020 Hansen et al.
2020/0113412 A1 4/2020 Jensen
2020/0121334 A1 4/2020 Galdonik et al.
2020/0129741 A1 4/2020 Kawwas et al.
2020/0324079 A1 10/2020 Jalgaonkar et al.
2021/0022843 A1 1/2021 Hauser
2021/0038385 A1 2/2021 Popp et al.
2021/0113224 A1 4/2021 Dinh
2021/0128182 A1 5/2021 Teigen et al.
2021/0137667 A1 5/2021 Sonnette et al.
2021/0138194 A1 5/2021 Carrison et al.
2021/0154433 A1 5/2021 Casey et al.
2021/0186537 A1 6/2021 Buck et al.
2021/0186541 A1 6/2021 Thress
2021/0205577 A1 7/2021 Jalgaonkar et al.
2021/0236148 A1 8/2021 Marchand et al.
2021/0290925 A1 9/2021 Merritt et al.
2021/0315598 A1 10/2021 Buck et al.
2021/0316127 A1 10/2021 Buck et al.
2021/0330344 A1 10/2021 Rosenbluth et al.
2021/0378694 A1 12/2021 Thress et al.
2021/0393278 A1 12/2021 O'Malley et al.
2021/0404464 A1 12/2021 Patoskie
2022/0000505 A1 1/2022 Hauser
2022/0000506 A1 1/2022 Hauser
2022/0000507 A1 1/2022 Hauser
2022/0015798 A1 1/2022 Marchand et al.
2022/0021197 A1 1/2022 Zhao et al.
2022/0022898 A1 1/2022 Cox et al.
2022/0033888 A1 2/2022 Schnall-Levin et al.
2022/0039815 A1 2/2022 Thress et al.
2022/0125451 A1 4/2022 Hauser
2022/0142638 A1 5/2022 Enright et al.
2022/0151647 A1 5/2022 Dolendo et al.
2022/0152355 A1 5/2022 Dolendo et al.
2022/0160381 A1 5/2022 Hauser
2022/0160382 A1 5/2022 Hauser
2022/0160383 A1 5/2022 Hauser
2022/0211400 A1 7/2022 Cox et al.
2022/0211992 A1 7/2022 Merritt et al.
2022/0226555 A1 7/2022 Sunenshine et al.
2022/0240959 A1 8/2022 Quick
2022/0296797 A1 9/2022 Chawla
2022/0331554 A1 10/2022 Beasley et al.
2022/0346800 A1 11/2022 Merritt et al.
2022/0346813 A1 11/2022 Quick
2022/0346814 A1 11/2022 Quick
2022/0347455 A1 11/2022 Merritt et al.
2022/0362512 A1 11/2022 Quick et al.
2022/0370761 A1 11/2022 Chou et al.
2022/0378445 A1 12/2022 Culbert et al.
2022/0378446 A1 12/2022 Culbert et al.
2022/0378447 A1 12/2022 Culbert et al.
2022/0378448 A1 12/2022 Culbert et al.
2022/0378451 A1 12/2022 Goyal et al.
2022/0378460 A1 12/2022 Culbert et al.
2022/0387072 A1 12/2022 Look et al.
2023/0015259 A1 1/2023 Buck et al.
2023/0046775 A1 2/2023 Quick
2023/0047682 A1 2/2023 Deaton et al.
2023/0052964 A1 2/2023 Singh et al.
2023/0059721 A1 2/2023 Chou et al.
2023/0062809 A1 3/2023 Merritt et al.
2023/0070120 A1 3/2023 Cox et al.
2023/0122587 A1 4/2023 Chou et al.
2023/0149034 A1 5/2023 Aklog et al.
2023/0200970 A1 6/2023 Merritt et al.
2023/0210554 A1 7/2023 Bruzzi et al.
2023/0218310 A1 7/2023 Scheinblum et al.
2023/0218313 A1 7/2023 Rosenbluth et al.
2023/0218383 A1 7/2023 Merritt et al.
2023/0233311 A1 7/2023 Merritt et al.
2023/0240705 A1 8/2023 Rosenbluth et al.
2023/0240706 A1 8/2023 Rosenbluth et al.
2023/0241302 A1 8/2023 Merritt et al.
2023/0248380 A1 8/2023 Long et al.
2023/0248498 A1 8/2023 Buck et al.
2023/0248499 A1 8/2023 Buck et al.
2023/0248500 A1 8/2023 Buck et al.
2023/0248501 A1 8/2023 Buck et al.
2023/0248502 A1 8/2023 Buck et al.
2023/0248503 A1 8/2023 Buck et al.
2023/0248504 A1 8/2023 Buck et al.
2023/0270991 A1 8/2023 Merritt et al.
2023/0310137 A1 10/2023 Merritt et al.
2023/0310138 A1 10/2023 Merritt et al.
2023/0310751 A1 10/2023 Merritt et al.
2023/0320834 A1 10/2023 Merritt et al.
2023/0329734 A1 10/2023 Marchand et al.
2023/0338130 A1 10/2023 Merritt et al.
2023/0338131 A1 10/2023 Merritt et al.
2023/0355256 A1 11/2023 Dinh
2023/0355259 A1 11/2023 Marchand et al.
2023/0355371 A1 11/2023 Buck et al.
2023/0355938 A1 11/2023 Merritt et al.

(56) References Cited

U.S. PATENT DOCUMENTS

| | | | |
|---|---|---|---|
| 2023/0363776 A1 | 11/2023 | Quick | |
| 2023/0363883 A1 | 11/2023 | Merritt et al. | |
| 2023/0389932 A1 | 12/2023 | Ozenne et al. | |
| 2023/0390045 A1 | 12/2023 | Merritt et al. | |
| 2024/0016505 A1 | 1/2024 | Horowitz et al. | |
| 2024/0016993 A1 | 1/2024 | Haslam et al. | |
| 2024/0058113 A1 | 2/2024 | Strauss et al. | |
| 2024/0074771 A1 | 3/2024 | Quick et al. | |
| 2024/0082540 A1 | 3/2024 | Brodt et al. | |
| 2024/0108366 A1 | 4/2024 | Horowitz et al. | |
| 2024/0131235 A1 | 4/2024 | Horowitz et al. | |
| 2024/0157041 A1 | 5/2024 | Zikry et al. | |
| 2024/0173042 A1 | 5/2024 | Yang et al. | |
| 2024/0198072 A1 | 6/2024 | Merritt et al. | |
| 2024/0207593 A1 | 6/2024 | Merritt et al. | |
| 2024/0245501 A1 | 7/2024 | Strauss et al. | |
| 2024/0245502 A1 | 7/2024 | Merritt et al. | |
| 2024/0261492 A1 | 8/2024 | Yang et al. | |
| 2024/0285387 A1 | 8/2024 | Merritt et al. | |
| 2024/0299053 A1 | 9/2024 | Hauser | |
| 2024/0307082 A1 | 9/2024 | Marchand et al. | |
| 2024/0307166 A1 | 9/2024 | Merritt et al. | |
| 2024/0341779 A1 | 10/2024 | Dinh | |
| 2024/0341788 A1 | 10/2024 | Cox et al. | |

FOREIGN PATENT DOCUMENTS

| | | | |
|---|---|---|---|
| CN | 102316809 | | 1/2012 |
| CN | 103764049 | | 4/2014 |
| CN | 103932756 | | 7/2014 |
| CN | 104068910 | | 10/2014 |
| CN | 106178227 | | 12/2016 |
| CN | 106470728 | | 3/2017 |
| CN | 108348319 | | 7/2018 |
| CN | 110312481 | | 10/2019 |
| CN | 110652645 | | 1/2020 |
| CN | 111281482 | | 6/2020 |
| DE | 1116001 | | 10/1961 |
| DE | 102017004383 | | 7/2018 |
| EP | 0914807 | | 5/1999 |
| EP | 1254634 | | 11/2002 |
| EP | 1991138 | | 11/2008 |
| EP | 2073864 | | 7/2009 |
| EP | 2203209 | | 7/2010 |
| EP | 2209509 | | 7/2010 |
| EP | 2394680 | | 12/2011 |
| EP | 1867290 | | 2/2013 |
| EP | 2624905 | | 8/2013 |
| EP | 2540328 | | 10/2013 |
| EP | 2726135 | | 5/2014 |
| EP | 2908783 | | 8/2015 |
| EP | 2939704 | | 11/2015 |
| EP | 2942624 | | 11/2015 |
| EP | 2967614 | | 1/2016 |
| EP | 2977072 | | 1/2016 |
| EP | 2367482 | | 10/2016 |
| EP | 3102274 | | 12/2016 |
| EP | 3122412 | | 2/2017 |
| EP | 3202340 | | 8/2017 |
| EP | 3302624 | | 4/2018 |
| EP | 3305220 | | 4/2018 |
| EP | 3305221 | | 4/2018 |
| EP | 3311875 | | 4/2018 |
| EP | 2231256 | | 5/2018 |
| EP | 3344157 | | 7/2018 |
| EP | 3417893 | | 12/2018 |
| EP | 3419528 | | 1/2019 |
| EP | 3422963 | | 1/2019 |
| EP | 3439561 | | 2/2019 |
| EP | 3449967 | | 3/2019 |
| EP | 3544528 | | 10/2019 |
| EP | 3583972 | | 12/2019 |
| EP | 3589348 | | 1/2020 |
| EP | 3603690 | | 2/2020 |
| EP | 3612264 | | 2/2020 |
| EP | 3620204 | | 3/2020 |
| EP | 3013404 | | 4/2020 |
| EP | 4039205 | | 8/2022 |
| EP | 4072613 | | 10/2022 |
| EP | 4076611 | | 10/2022 |
| EP | 4079344 | | 10/2022 |
| EP | 4137070 | | 2/2023 |
| EP | 4144310 | | 3/2023 |
| EP | 4252992 | | 10/2023 |
| EP | 4419159 | | 8/2024 |
| GB | 1588072 | | 4/1981 |
| GB | 2498349 | | 7/2013 |
| JP | H6190049 | | 7/1994 |
| JP | H07323090 | A | 12/1995 |
| JP | 2001522631 | | 5/1999 |
| JP | 2000175925 | | 6/2000 |
| JP | 2004097807 | | 4/2004 |
| JP | 2005511989 | | 4/2005 |
| JP | 2005-095242 | | 6/2005 |
| JP | 2005230132 | | 9/2005 |
| JP | 2005323702 | | 11/2005 |
| JP | 2006094876 | | 4/2006 |
| JP | 2007-222658 | | 9/2007 |
| JP | 2011526820 | | 1/2010 |
| JP | 2011517424 | | 6/2011 |
| JP | 05694718 | | 4/2015 |
| JP | 2015208685 | | 11/2015 |
| JP | 2016513505 | | 5/2016 |
| JP | 2016104212 | | 6/2016 |
| JP | 2017533051 | | 11/2017 |
| JP | 2018525088 | | 9/2018 |
| JP | 2003033359 | | 2/2023 |
| JP | 7253376 | | 3/2023 |
| JP | 7324264 | | 8/2023 |
| JP | 7491974 | | 5/2024 |
| WO | WO1997017889 | | 5/1997 |
| WO | WO9833443 | | 8/1998 |
| WO | WO9838920 | | 9/1998 |
| WO | WO9839053 | | 9/1998 |
| WO | WO9851237 | | 11/1998 |
| WO | WO1999044542 | | 9/1999 |
| WO | WO0032118 | | 6/2000 |
| WO | WO2000053120 | | 9/2000 |
| WO | WO0202162 | | 1/2002 |
| WO | WO2002055146 | | 7/2002 |
| WO | WO03015840 | | 2/2003 |
| WO | WO2004018916 | | 3/2004 |
| WO | WO2004093696 | | 11/2004 |
| WO | WO2005046736 | | 5/2005 |
| WO | WO2006029270 | | 3/2006 |
| WO | WO2006110186 | | 10/2006 |
| WO | WO2006124307 | | 11/2006 |
| WO | WO2007092820 | | 8/2007 |
| WO | WO2009082513 | | 7/2009 |
| WO | WO2009086482 | | 7/2009 |
| WO | WO2009126747 | | 10/2009 |
| WO | WO2009155571 | | 12/2009 |
| WO | WO2010002549 | | 1/2010 |
| WO | WO2010010545 | | 1/2010 |
| WO | WO2010023671 | | 3/2010 |
| WO | WO2010049121 | | 5/2010 |
| WO | WO2010095712 | | 8/2010 |
| WO | WO2010102307 | | 9/2010 |
| WO | WO2011032712 | | 3/2011 |
| WO | WO2011054531 | | 5/2011 |
| WO | WO2011073176 | | 6/2011 |
| WO | WO2012009675 | | 1/2012 |
| WO | WO2012011097 | | 1/2012 |
| WO | WO2012049652 | | 4/2012 |
| WO | WO2012065748 | | 5/2012 |
| WO | WO2012114633 | | 8/2012 |
| WO | WO2012120490 | | 9/2012 |
| WO | WO2012162437 | | 11/2012 |
| WO | WO2014047650 | | 3/2014 |
| WO | WO2014081892 | | 5/2014 |
| WO | WO2014139845 | | 9/2014 |
| WO | WO2015006782 | | 1/2015 |
| WO | WO2015061365 | | 4/2015 |
| WO | WO2015121424 | | 8/2015 |

(56) References Cited

FOREIGN PATENT DOCUMENTS

| | | |
|---|---|---|
| WO | WO2015179329 | 11/2015 |
| WO | WO2015189354 | 12/2015 |
| WO | WO2015191646 | 12/2015 |
| WO | WO2016014955 | 1/2016 |
| WO | WO2016071524 | 5/2016 |
| WO | WO2017024258 | 2/2017 |
| WO | WO2017033182 | 3/2017 |
| WO | WO2017058280 | 4/2017 |
| WO | WO2017070702 | 4/2017 |
| WO | WO2017106877 | 6/2017 |
| WO | WO2017189535 | 11/2017 |
| WO | WO2017189550 | 11/2017 |
| WO | WO2017189591 | 11/2017 |
| WO | WO2017189615 | 11/2017 |
| WO | WO2017210487 | 12/2017 |
| WO | WO2018049317 | 3/2018 |
| WO | WO2018065092 | 4/2018 |
| WO | WO2018080590 | 5/2018 |
| WO | WO2018148174 | 8/2018 |
| WO | WO2019010318 | 1/2019 |
| WO | WO2019050765 | 3/2019 |
| WO | WO2019064306 | 4/2019 |
| WO | WO2019075444 | 4/2019 |
| WO | WO2019094456 | 5/2019 |
| WO | WO2019173475 | 9/2019 |
| WO | WO2019222117 | 11/2019 |
| WO | WO2019246240 | 12/2019 |
| WO | WO2020036809 | 2/2020 |
| WO | WO2020142381 | 7/2020 |
| WO | WO2021067134 | 4/2021 |
| WO | WO2021076954 | 4/2021 |
| WO | WO2021127202 | 6/2021 |
| WO | WO2021248042 | 12/2021 |
| WO | WO2022032173 | 2/2022 |
| WO | WO2022103848 | 5/2022 |
| WO | WO2022109021 | 5/2022 |
| WO | WO2022109034 | 5/2022 |
| WO | WO2023018819 | 2/2023 |
| WO | WO2023069874 | 4/2023 |
| WO | WO2003048616 | 6/2023 |
| WO | WO2023115032 | 6/2023 |
| WO | WO2023137341 | 7/2023 |
| WO | WO2023147353 | 8/2023 |
| WO | WO2023154612 | 8/2023 |
| WO | WO2023192925 | 10/2023 |
| WO | WO2023215779 | 11/2023 |
| WO | WO2024103036 | 5/2024 |
| WO | WO2024151629 | 7/2024 |

OTHER PUBLICATIONS

US 12,115,056 B2, 10/2024, Merritt et al. (withdrawn)

International Search Report and Written Opinion for International App. No. PCT/US2023/079428; Applicant: Inari Medical, Inc., Date of Mailing: May 29, 2024, 18 pages.

Extended European Search Report for European Application No. 21818772.2, Applicant: Inari Medical, Inc., Date of Mailing: May 10, 9 pages.

Chinese Office Action received for Application No. 202111061740.2, Applicant: Inari Medical, Inc, Date of Mailing: May 23, 2024, 15 pages.

English translation of Japanese Office Action mailed Jun. 25, 2024 for Japanese Application No. 2022-574456, 5 pages.

Japanese Office Action mailed Jul. 8, 2024 for Japanese Application No. 2022-522892, 14 pages.

Chinese first Office Action mailed May 10, 2024 for Chinese Application No. 202080087833.X, 11 pages.

Partial Supplementary European Search Report received for European Application No. 21852966.7; Applicant: Inari Medical, Inc., Date of Mailing: Jul. 23, 2024, 12 pages.

Japanese Office Action mailed Aug. 2, 2024 for Japanese Application No. 2023-213724, 3 pages.

English Translation of Japanese Office Action mailed Jul. 23, 2024 for Japanese Application No. 2022-535535, 11 pages.

Extended European Search Report received for European Application No. 21895504.5; Applicant: Inari Medical, Inc., Date of Mailing: Aug. 16, 2024, 10 pages.

International Search Report and Written Opinion for International App. No. PCT/US2024/010875; Applicant: Inari Medical, Inc., Date of Mailing: Apr. 26, 2024, 15 pages.

English translation of Japanese Office Action mailed Sep. 17, 2024 for Japanese Application No. 2023-203650, 6 pages.

English machine translation of Japanese Office Action mailed Oct. 10, 2024 for Japanese Application No. 2022-522892, 11 pages.

Gibbs, et al., "Temporary Stent as a bail-out device during percutaneous transluminal coronary angioplasty: preliminary clinical experience," British Heart Journal, 1994, 71:372-377, Oct. 12, 1993, 6 pgs.

Gupta, S. et al., "Acute Pulmonary Embolism Advances in Treatment", JAPI, Association of Physicians India, Mar. 2008, vol. 56, 185-191.

International Search Report and Written Opinion for International App. No. PCT/US13/61470, mailed Jan. 17, 2014, 7 pages.

International Search Report and Written Opinion for International App. No. PCT/US2014/046567, mailed Nov. 3, 2014, 13 pages.

International Search Report and Written Opinion for International App. No. PCT/US2014/061645, mailed Jan. 23, 2015, 15 pages.

International Search Report for International App. No. PCT/US13/71101, mailed Mar. 31, 2014, 4 pages.

Konstantinides, S. et al., "Pulmonary embolism hotline 2012—Recent and expected trials", Thrombosis and Haemostasis, Jan. 9, 2013:33; 43-50.

Konstantinides, S. et al., "Pulmonary embolism: risk assessment and management", European Society of Cardiology; European Heart Journal, Sep. 7, 2012:33, 3014-3022.

Kucher, N. et al., "Percutaneous Catheter Thrombectomy Device for Acute Pulmonary Embolism: In Vitro and in Vivo Testing", Circulation, Sep. 2005:112:e28-e32.

Kucher, N., "Catheter Interventions in Massive Pulmonary Embolism", Cardiology Rounds, Mar. 2006 vol. 10, Issue 3, 6 pages.

Kucher, N. et al., "Management of Massive Pulmonary Embolism", Radiology, Sep. 2005:236:3 852-858.

Kucher, N. et al., "Randomized, Controlled Trial of Ultrasound-Assisted Catheter-Directed Thrombolysis for Acute Intermediate-Risk Pulmonary Embolism." Circulation, 2014, 129, pp. 9 pages.

Kuo, W. et al., "Catheter-directed Therapy for the Treatment of Massive Pulmonary Embolism: Systematic Review and Meta-analysis of Modern Techniques", Journal of Vascular and Interventional Radiology, Nov. 2009:20:1431-1440.

Kuo, W. et al., "Catheter-Directed Embolectomy, Fragmentation, and Thrombolysis for the Treatment of Massive Pulmonary Embolism After Failure of Systemic Thrombolysis", American College of CHEST Physicians 2008: 134:250-254.

Kuo, W. Md, "Endovascular Therapy for Acute Pulmonary Embolism", Continuing Medical Education Society of Interventional Radiology ("CME"); Journal of Vascular and Interventional Radiology, Feb. 2012: 23:167-179.

Lee, L. et al, "Massive pulmonary embolism: review of management strategies with a focus on catheter-based techniques", Expert Rev. Cardiovasc. Ther. 8(6), 863-873 (2010).

Liu, S. et al, "Massive Pulmonary Embolism: Treatment with the Rotarex Thrombectomy System", Cardiovascular Interventional Radiology; 2011: 34:106-113.

Muller-Hulsbeck, S. et al. "Mechanical Thrombectomy of Major and Massive Pulmonary Embolism with Use of the Amplatz Thrombectomy Device", Investigative Radiology, Jun. 2001:36:6:317-322.

Reekers, J. et al., "Mechanical Thrombectomy for Early Treatment of Massive Pulmonary Embolism", CardioVascular and Interventional Radiology, 2003: 26:246-250.

Schmitz-Rode et al., "New Mesh Basket for Percutaneous Removal of Wall-Adherent Thrombi in Dialysis Shunts," Cardiovasc Intervent Radiol 16:7-10 1993 4 pgs.

(56) References Cited

OTHER PUBLICATIONS

Schmitz-Rode et al., "Temporary Pulmonary Stent Placement as Emergency Treatment of Pulmonary Embolism," Journal of the American College of Cardiology, vol. 48, No. 4, 2006 (5 pgs.).
Schmitz-Rode, T. et al., "Massive Pulmonary Embolism: Percutaneous Emergency Treatment by Pigtail Rotation Catheter", JACC Journal of the American College of Cardiology, Aug. 2000:36:2:375-380.
Spiotta, A et al., "Evolution of thrombectomy approaches and devices for acute stroke: a technical review." J NeuroIntervent Surg 2015, 7, pp. 7 pages.
Svilaas, T. et al., "Thrombus Aspiration During Primary Percutaneous Coronary Intervention." The New England Journal of Medicine, 2008, vol. 358, No. 6, 11 pages.
Tapson, V., "Acute Pulmonary Embolism", The New England Journal of Medicine, Mar. 6, 2008:358:2037-52.
The Penumbra Pivotal Stroke Trial Investigators, "The Penumbra Pivotal Stroke Trial: Safety and Effectiveness of a New Generation of Mechanical Devices for Clot Removal in Intracranial Large Vessel Occlusive Disease." Stroke, 2009, 40: p. 9 pages.
Truong et al., "Mechanical Thrombectomy of Iliocaval Thrombosis Using a Protective Expandable Sheath," Cardiovasc Intervent Radiol27-254-258, 2004, 5 pgs.
Turk et al., "Adapt Fast study: a direct aspiration first pass technique for acute stroke thrombectomy." J NeuroIntervent Surg, vol. 6, 2014, 6 pages.
Uflacker, R., "Interventional Therapy for Pulmonary Embolism", Journal of Vascular and Interventional Radiology, Feb. 2001: 12:147-164.
Verma, R., Md et al. "Evaluation of a Newly Developed Percutaneous Thrombectomy Basket Device in Sheep With Central Pulmonary Embolisms", *Investigative Radiology*, Oct. 2006, 41, 729-734.
International Search Report and Written Opinion for International App. No. PCT/US2015/034987 filed Jun. 9, 2015, Applicant: Inceptus Medical, LLC, Date of Mailing: Sep. 17, 2015, 12 pages.
International Search Report and Written Opinion for International App. No. PCT/US2016/067628 filed Dec. 19, 2016, Applicant: Inari Medical, Inc., Date of Mailing: Apr. 10, 2017, 11 pages.
Goldhaber, S et al. "Percutaneous Mechanical Thrombectomy for Acute Pulmonary Embolism - A Double-Edged Sword," American College of CHEST Physicians, Aug. 2007, 132:2, 363-372.
Goldhaber, S., "Advanced treatment strategies for acute pulmonary embolism, including thrombolysis and embolectomy," Journal of Thrombosis and Haemostasis, 2009: 7 (Suppl. 1): 322-327.
International Search Report and Written Opinion for International App. No. PCT/US2017/029696, Date of Filing: Apr. 26, 2017, Applicant: Inari Medical, Inc., Date of Mailing: Sep. 15, 2017, 19 pages.
International Search Report and Written Opinion for International App. No. PCT/US2016/058536, Date of Filing: Oct. 24, 2016, Applicant: Inari Medical, Inc., Date of Mailing: Mar. 13, 2017, 14 pages.
International Search Report and Written Opinion for International App. No. PCT/US2018/048786, Date of Filing: Aug. 30, 2018, Applicant: Inari Medical, Inc., Date of Mailing: Dec. 13, 2018, 12 pages.
International Search Report and Written Opinion for International App. No. PCT/US2018/055780, Date of Filing: Oct. 13, 2018, Applicant: Inceptus Medical LLC., Date of Mailing: Jan. 22, 2019, 8 pages.
International Search Report and Written Opinion for International App. No. PCT/US2019/045794, Date of Filing: Aug. 8, 2019, Applicant: Inari Medical, Inc., Date of Mailing: Nov. 1, 2019, 17 pages.
International Search Report and Written Opinion for International App. No. PCT/US2020/056067, Date of Filing: Oct. 16, 2020; Applicant: Inari Medical, Inc., Date of Mailing: Jan. 22, 2021, 8 pages.
International Search Report and Written Opinion for International App. No. PCT/US2020/055645, Date of Filing: Dec. 17, 2020; Applicant: Inari Medical, Inc., Date of Mailing: Apr. 14, 2021, 12 pages.
Vorwerk, D. Md, et al., "Use of a Temporary Caval Filter to Assist Percutaneous Iliocaval Thrombectomy: Experimental Results." SCVIR, 1995, 4 pages.
Wikipedia; Embolectomy; retrieved from the internet: https://en.wikipedia.org/wiki/Embolectomy; 4 pgs.; retrieved/printed: Mar. 24, 2016.
O'Sullivan; Thrombolysis versus thrombectomy in acute deep vein thrombosis; Interventional Cardiology; 3(5); pp. 589-596; Oct. 2011.
Capture Vascular Systems; (company website); retrieved from the internet: http://www.capturevascular.com; 3 pgs.; retrieved/printed: Mar. 24, 2016.
Edwards Lifesciences; Fogarty® Occlusion Catheters (product brochure); retrieved from the internet: http://web.archive.org/web/20150228193218/http://www.edwards.com/products/vascular/atraumaticocclusion/pages/occlusioncatheter.aspx; © 2011; 2 pgs.; retrieved/printed: Mar. 24, 2011.
Boston Scientific; Fetch(TM) 2 Aspiration Catheter (product information); retrieved from the internet: http://www.bostonscientific.com/en-US/products/thrombectomy-systems/fetch2-aspiration-catheter.html; 2 pgs.; retrieved/printed: Mar. 24, 2016.
Penumbra, Inc.; Indigo® System (product information); retrieved from the internet: http://www.penumbrainc.com/peripherallpercutaneous-thromboembolectomy/indigo-system; 7 pgs.; retrieved/printed: Mar. 24, 2016.
YOUTUBE; Merci Retrieval System X Series Animation; uploaded Mar. 16, 2009 (product information); posted on May 7, 2009 by SSMDePAUL, time 1:09, retrieved from the internet: https://www.youtube.com/watch?v=MGX7deuFkhc; 3 pgs.; retrieved/printed: Mar. 24, 2016.
Covidien; Solitaire(TM) AS Neurovascular Remodeling Device (product information); retrieved from the internet: http://www.ev3.net/neuro/intl/remodeling-devices/solitaire-ab. htm; © 2015; 2 pgs.; retrieved/printed: Mar. 24, 2016.
International Search Report and Written Opinion for International App. No. PCT/US21/35965, Date of Filing: Jun. 4, 2021, Applicant Inari Medical, Inc., Date of Mailing: Sep. 28, 2021, 12 pages.
International Search Report and Written Opinion for International App. No. PCT/US21/45072 Date of Filing: Aug. 6, 2021, Applicant: Inari Medical, Inc., Date of Mailing: Jan. 20, 2022, 10 pages.
International Search Report and Written Opinion for International App. No. PCT/US21/58793; Date of Filing: Nov. 10, 2021, Applicant: Inari Medical, Inc., Date of Mailing: Mar. 16, 2022, 13 pages.
International Search Report and Written Opinion for International App. No. PCT/US21/59718; Date of Filing: Nov. 17, 2021, Applicant: Inari Medical, Inc., Date of Mailing: Mar. 22, 2022, 13 pages.
International Search Report and Written Opinion for International App. No. PCT/US21/59735; Date of Filing: Nov. 17, 2021, Applicant: Inari Medical, Inc., Date of Mailing: Mar. 22, 2022, 11 pages.
International Search Report and Written Opinion for International App. No. PCT/US23/60502; Date of Filing: Jan. 11, 2023, Applicant: Inari Medical, Inc., Date of Mailing: May 25, 2023, 9 pages.
International Search Report and Written Opinion for International App. No. PCT/US23/61256; Date of Filing: Jan. 25, 2023, Applicant: Inari Medical, Inc., Date of Mailing: Jun. 7, 2023, 8 pages.
Gross et al., "Dump the pump: manual aspiration thrombectomy (MAT) with a syringe is technically effective, expeditious, and cost-efficient," J NeuroIntervent Surg, 2018, 4 pages.
English translation of Japanese Office Action mailed Jun. 7, 2023 for Japanese Application No. 2021-507564, 7 pages.
European Office Action received for EP Application No. 16876941.2, Applicant: Inari Medical, Inc, Date of Mailing: Jul. 18, 2023, 6 pages.
International Search Report and Written Opinion for International App. No. PCT/US23/60927; Date of Filing: Jan. 19, 2023, Applicant: Inari Medical, Inc., Date of Mailing: Jul. 20, 2023, 12 pages.
Extended European Search Report issued for EP Application No. 20877370.5, Date of Mailing: Oct. 17, 2023, 11 pages.

(56) References Cited

OTHER PUBLICATIONS

International Search Report and Written Opinion for International App. No. PCT/US23/65128; Date of Filing: Mar. 30, 2023, Applicant: Inari Medical, Inc., Date of Mailing: Nov. 14, 2023, 14 pages.
International Search Report and Written Opinion for International App. No. PCT/US23/66538; Date of Filing: May 3, 2023, Applicant: Inari Medical, Inc., Date of Mailing: Jan. 4, 2024, 14 pages.
English translation of Japanese Office Action received for JP Application No. 2022-574456, Applicant: Inari Medical, Inc, Date of Mailing: Jan. 23, 2024, 12 pages.
Chinese First Office Action received for CN Application No. 201980067623.1, Applicant: Inari Medical, Inc., Date of Mailing: Jan. 31, 2024, 10 pages.
International Search Report and Written Opinion for International App. No. PCT/US23/73765; Date of Filing: Sep. 8, 2023, Applicant: Inari Medical, Inc., Date of Mailing: Feb. 28, 2024, 7 pages.
International Search Report and Written Opinion for International App. No. PCT/US23/69892; Date of Filing: Jul. 10, 2023, Applicant: Inari Medical, Inc., Date of Mailing: Feb. 29, 2024, 12 pages.

* cited by examiner

CATHETER FOR USE WITH CLOT TREATMENT SYSTEMS

CROSS-REFERENCE TO RELATED APPLICATION

The present application claims priority to U.S. Provisional App. No. 63/437,885, filed Jan. 9, 2023, and titled "CATHETER FOR USE WITH CLOT TREATMENT SYSTEMS," which is incorporated herein by reference in its entirety.

TECHNICAL FIELD

The present technology generally relates to thrombectomy catheters for use with clot treatment systems, and associated devices and methods.

BACKGROUND

Thromboembolic events are characterized by an occlusion of a blood vessel. Thromboembolic disorders, such as stroke, pulmonary embolism, heart attack, peripheral thrombosis, atherosclerosis, and the like, affect many people. These disorders are a major cause of morbidity and mortality.

When an artery is occluded by a clot, tissue ischemia develops. The ischemia will progress to tissue infarction if the occlusion persists. However, infarction does not develop or is greatly limited if the flow of blood is reestablished rapidly. Failure to reestablish blood flow can accordingly lead to the loss of limb, angina pectoris, myocardial infarction, stroke, or even death.

In the venous circulation, occlusive material can also cause serious harm. Blood clots can develop in the large veins of the legs and pelvis, a common condition known as deep venous thrombosis (DVT). DVT commonly occurs where there is a propensity for stagnated blood (e.g., long-distance air travel, immobility, etc.) and clotting (e.g., cancer; recent surgery, such as orthopedic surgery, etc.). DVT can obstruct drainage of venous blood from the legs, leading to swelling, ulcers, pain, and infection. DVT can also create a reservoir in which blood clots can collect and then travel to other parts of the body, including the heart, lungs, brain (which may cause a stroke), abdominal organs, and/or extremities.

Various thrombectomy devices exist for removing occlusive material (e.g., blood clots) to reestablish blood flow within a patient. Thrombectomy devices typically have a catheter containing a mechanical clot treatment component for engaging and removing occlusive material lodged in a blood vessel. Such thrombectomy devices are often delivered intravascularly to the occlusive material over a guidewire, which often extends through the entire length of the catheter's lumen. The guidewire can be too short for some procedures such that there is insufficient length on the guidewire to deliver the thrombectomy device to the occlusive material. Additionally, long thrombectomy devices can require excessive time for exchanges over the guidewire. This can complicate the thrombectomy procedure, such as inadequately removing the occlusive material or otherwise failing to reestablish sufficient blood flow within the patient.

BRIEF DESCRIPTION OF THE DRAWINGS

Many aspects of the present technology can be better understood with reference to the following drawings. The accompanying Figures depict embodiments of the present technology and are not intended to be limiting of its scope unless expressly indicated. The sizes of various depicted elements are not necessarily drawn to scale, and these various elements may be enlarged to improve legibility. Component details may be abstracted in the Figures to exclude details such as the position of components and certain precise connections between such components when such details are unnecessary for a complete understanding of how to make and use the present technology. Furthermore, components can be shown as transparent in certain views for clarity of illustration only and not to indicate that the component is necessarily transparent. Many of the details, dimensions, angles, and other features shown in the Figures are merely illustrative of particular embodiments of the disclosure. Accordingly, other embodiments can have other details, dimensions, angles, and features without departing from the present technology. In addition, those of ordinary skill in the art will appreciate that further embodiments of the present technology can be practiced without several of the details described below.

DETAILED DESCRIPTION

Figure 1A:
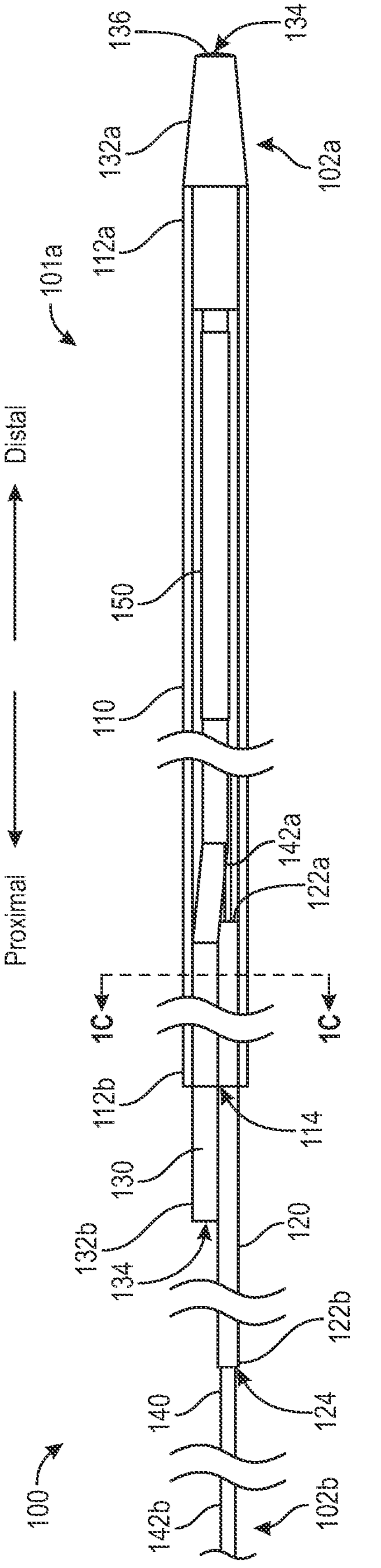
FIGS. 1A and 1B are side views of a clot treatment catheter in a first configuration and a second configuration, respectively, in accordance with embodiments of the present technology.

The present technology is generally directed to thrombectomy catheters for use with clot treatment systems, and associated devices and methods. In some of the embodiments described in detail below, a thrombectomy catheter ("catheter") can include an outer sheath, an outer sheath drive component operably coupled to the outer sheath, a guidewire sheath slidably disposed within the outer sheath, and a guidewire sheath drive component operably coupled to the guidewire sheath and slidably disposed within the outer sheath drive component. Additionally, the catheter can include a clot treatment component. The clot treatment component can be coupled to the guidewire sheath and positionable within the outer sheath. In these and other embodiments, the catheter can include at least one clot treatment drive component operably coupled to the clot treatment component. The clot treatment drive component can be positioned between (e.g., radially between, telescopically between, and the like) the outer sheath drive component and the guidewire sheath drive component.

During a clot treatment procedure (e.g., removing occlusive material), the catheter can be transitioned between a first (e.g., sheathed) configuration in which the clot treatment component is contained within the outer sheath and a second (e.g., deployed) configuration in which the clot treatment component is deployed from within the outer sheath by moving the outer sheath and/or the guidewire sheath relative to each other. For example, to transition the catheter from the first configuration to the second configuration, a user can move the guidewire sheath drive component in a first direction (e.g., distally, a distal direction) relative to the outer sheath to cause a corresponding movement of the guidewire sheath and thereby extend at least a portion of the guidewire sheath outwardly from within the outer sheath. The clot treatment component can be coupled to or positioned around the portion of the guidewire sheath such that extending this portion of the guidewire sheath outwardly from within the outer sheath can allow the clot treatment component to expand or be deployed. Additionally, or alternatively, to transition the catheter from the first configuration to the second configuration, the user can move the outer sheath drive component in a second direction (e.g., proximally) relative to the guidewire sheath to cause a corresponding movement of the outer sheath and thereby withdraw the outer sheath over the guidewire sheath, e.g., to expose the portion of the guidewire sheath. To transition the catheter from the second configuration to the first configuration, the movement of the guidewire sheath drive component and/or the outer sheath drive component can be reversed, e.g., the user can move the guidewire sheath drive component in the second direction and/or the outer sheath drive component in the first direction.

The clot treatment component can be fully sheathed within the outer sheath in the first configuration, e.g., for delivery through a blood vessel to the site of an occlusion. In the second configuration, at least part of the clot treatment component can be deployed from or extend beyond the outer sheath. For example, in the second configuration the clot treatment component can be positioned for engaging an occlusion during a clot treatment. In some embodiments, the user can deploy, sheath, and/or change at least one dimension (e.g., length, width, diameter, cross-sectional area, and the like) and/or change at least one characteristic or mechanical property (e.g., radial force, tension, compression, shape, and the like) of the clot treatment component by moving the clot treatment drive component.

In some aspects of the present technology, the catheters can occupy a relatively short length of a guidewire, such that an increased length of the guidewire is available, for example, to allow additional clot treatment devices to be intravascularly delivered within the patient. This is expected to reduce at least some complications that may arise during clot treatment and/or removal procedures, such as when there is an insufficient length of the guidewire available for the user to adequately address the patient's clot. Additionally, or alternatively, at least some of the catheters are expected to be easier for a user to transition between configurations, such that the user can more readily/easily perform multiple passes at clot material during a procedure. For example, at least some of the catheters can be configured such that the clot treatment component can be completely or at least partially re-sheathed after the clot treatment component has been deployed. In these and other embodiments, the catheters of the present technology are expected to occupy and/or engage a shorter length of a guidewire compared to other clot treatment devices, which can enable the catheter to be more readily/easily loaded and unloaded from the guidewire when performing multiple passes at clot material within the patient.

Certain details are set forth in the following description and in FIGS. 1A-8 to provide a thorough understanding of various embodiments of the present technology. In other instances, well-known structures, materials, operations, and/or systems often associated with intravascular procedures, blood filtering, clot removal procedures, catheters, and the like are not shown or described in detail in the following disclosure to avoid unnecessarily obscuring the description of the various embodiments of the technology. Those of ordinary skill in the art will recognize, however, that the present technology can be practiced without one or more of the details set forth herein and/or with other structures, methods, components, and so forth. Moreover, although many of the devices and systems are described herein in the context of removing and/or treating clot material from a vessel, the present technology can be used to remove and/or treat any unwanted material within a vessel in addition or alternatively to clot material, such as thrombi, emboli, plaque, etc. Accordingly, the terms "clot" and "clot material" as used herein can refer to any of the foregoing materials within a vessel.

The terminology used below is to be interpreted in its broadest reasonable manner, even though it is being used in conjunction with a detailed description of certain examples of embodiments of the technology. Indeed, certain terms may even be emphasized below; however, any terminology intended to be interpreted in any restricted manner will be overtly and specifically defined as such in this Detailed Description section.

With regard to the terms "distal" and "proximal" within this description, unless otherwise specified, the terms can reference a relative position of the portions of a catheter subsystem with reference to an operator and/or a location in the vasculature. Also, as used herein, the designations "rearward," "forward," "upward," "downward," and the like are not meant to limit the referenced component to a specific orientation. It will be appreciated that such designations refer to the orientation of the referenced component as illustrated in the Figures; the systems of the present technology can be used in any orientation suitable to the user.

Figure 1B:
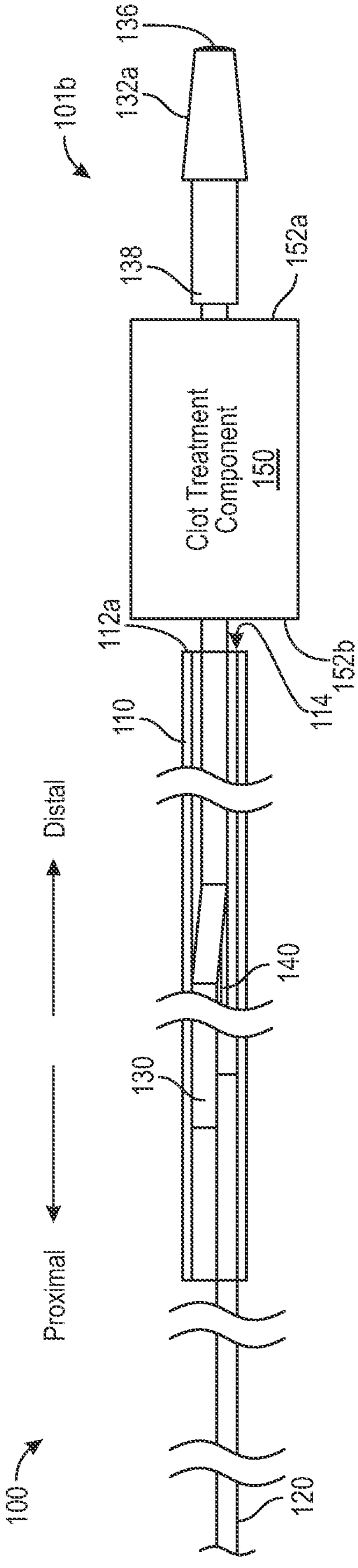
Figure 1C:
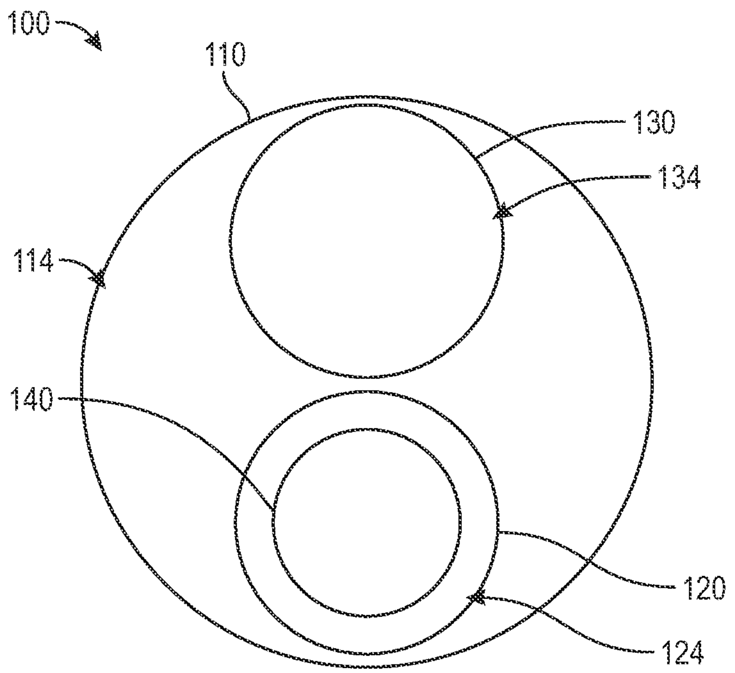
FIG. 1C is a partially-schematic cross-sectional view of the catheter of FIGS. 1A and 1B taken along line 1C-1C of FIG. 1A in accordance with embodiments of the present technology.
Figure 6A:
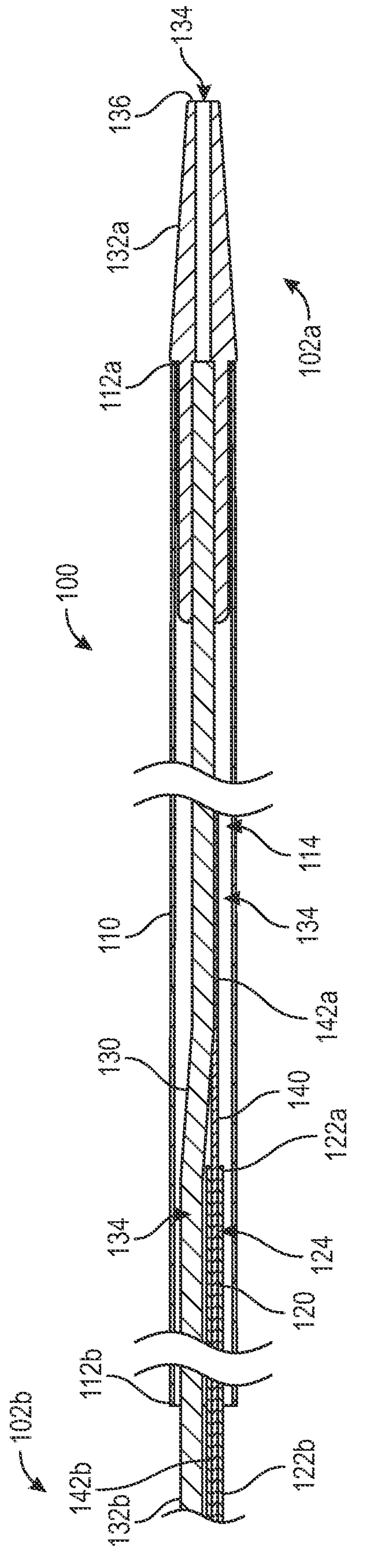
FIGS. 6A and 6B are side cross-sectional views of the clot treatment catheter of FIGS. 1A and 1B, respectively, in accordance with embodiments of the present technology.
Figure 6B:
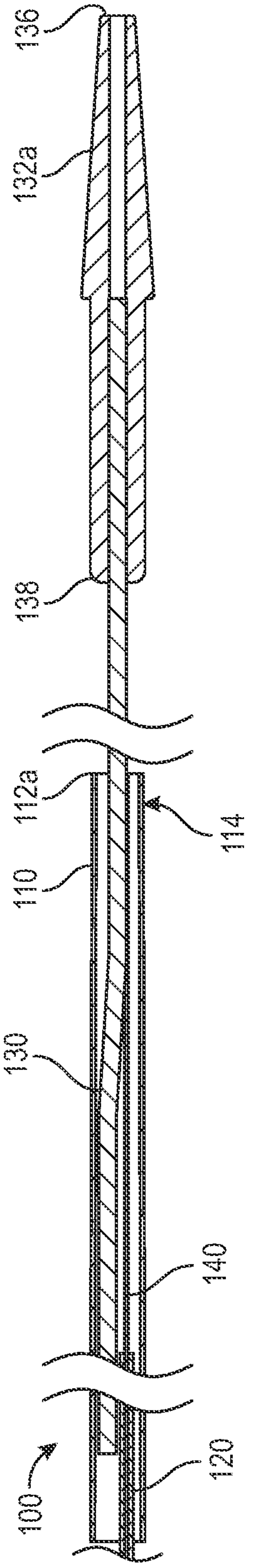

FIGS. 1A and 1B are side views of a clot treatment catheter ("catheter 100") in a first configuration 101*a* and a second configuration 101*b*, respectively, in accordance with embodiments of the present technology. FIG. 1C is a partially-schematic cross-sectional view of the catheter 100 taken along line 1C-1C of FIG. 1A in accordance with embodiments of the present technology. FIGS. 6A and 6B are cross-sectional views of the catheter 100 in the first configuration 101*a* and the second configuration 101*b*, respectively, in accordance with embodiments of the present technology. In FIGS. 1A, 1B, 6A, and 6B, aspects of the catheter 100 are illustrated as transparent for clarity.

In some embodiments, the catheter 100 includes a first or distal end portion 102*a* and a second or proximal end portion

102*b* (the various ends/end portions described herein are not visible in the plane of FIG. 1C). During a clot treatment procedure, the catheter 100 can be advanced intravascularly to a treatment site within a blood vessel of a patient P. In at least some embodiments, for example, the catheter 100 is advanced though the vasculature until all or part of the clot treatment component 150 (not shown in FIGS. 6A and 6B) is positioned in or distal to clot material within the blood vessel.

The catheter 100 can include one or more sheaths and/or components. In some embodiments, the catheter 100 includes an outer sheath 110, an outer sheath drive component 120, a guidewire sheath 130, a guidewire sheath drive component 140, and a clot treatment component 150 (shown schematically). Referring to FIGS. 1A and 6A, the outer sheath 110 can include an elongated tube or member comprising a first or distal end portion 112*a*, a second or proximal end portion 112*b* opposite the distal end portion 112*a*, and a lumen 114 ("the outer sheath lumen 114") extending from the distal end portion 112*a* to the proximal end portion 112*b*. The outer sheath drive component 120 can include an elongated tube or member comprising a distal end portion 122*a*, a proximal end portion 122*b* opposite the distal end portion 122*a*, and a lumen 124 ("the outer sheath drive component lumen 124") extending from the distal end portion 122*a* to the proximal end portion 122*b*. At least part of the outer sheath drive component 120 (e.g., at least part of the distal end portion 122*a*) can be positioned within the outer sheath lumen 114 and coupled to the outer sheath 110. The proximal end portion 122*b* of the outer sheath drive component 120 can extend proximally from the proximal end portion 112*b* of the outer sheath 110 and/or can be integrated with a handle or other user interface, for example, to allow a user to grasp, manipulate, move, etc. the outer sheath drive component 120 to thereby move the outer sheath 110 relative to one or more other portions of the catheter 100.

The guidewire sheath 130 can be positioned at least partially within the outer sheath lumen 114, for example, proximate/adjacent to the outer sheath drive component 120. The guidewire sheath 130 can comprise a tube having a first or distal end or tip portion 132*a* ("distal tip 132*a*"), a second or proximal end portion 132*b*, and a lumen 134 ("guidewire sheath lumen 134") extending from the distal tip 132*a* to the proximal end portion 132*b*. The distal tip 132*a* can be integral with the guidewire sheath 130 or a separate component coupled to a distal end of the guidewire sheath 130. The distal tip 132*a* of the guidewire sheath 130 can define a distal terminus 136 of the catheter 100. The guidewire sheath lumen 134 can be configured to receive a guidewire (not shown) therethrough. In at least some embodiments, for example, the guidewire can be inserted within the guidewire sheath lumen 134 via the distal tip 132*a* and extend fully beyond the proximal end portion 132*b* of the guidewire sheath 130. The guidewire sheath 130 can be relatively short in length. For example, the guidewire sheath 130 can be shorter than an overall length of the catheter 100 between the distal and proximal end portions 102*a*, 102*b*. Additionally, or alternatively, the proximal end 122*b* of the outer sheath drive component 120 can extend proximally beyond the proximal end 132*b* of the guidewire sheath 130 in the first and second configurations 101*a*, 101*b*. In some aspects of the present technology, relatively short guidewire sheaths 130 are expected to allow an increased length of a guidewire to be available for intravascular delivery of additional clot treatment devices within a patient. This, in turn, can reduce intravascular crowding, improve intravascular navigability, and/or increase the amount of clot material that can be removed from the patient.

The guidewire sheath drive component 140 can be positioned at least partially within the outer sheath drive component lumen 124 and can be coupled to the guidewire sheath 130. The guidewire sheath drive component 140 can include an elongated shaft, tube, or member comprising a first or distal end portion 142*a* and a second or proximal end portion 142*b* opposite the distal end portion 142*a*. The distal end portion 142*a* of the guidewire sheath drive component 140 extends distally from the distal end portion 122*a* of the outer sheath drive component 120 and is coupled to the guidewire sheath 130, as shown and described in further detail with reference to FIGS. 2A and 2B. The proximal end portion 142*b* can extend proximally from the proximal end portion 122*b* of the outer sheath drive component 120 and/or can be integrated with a handle or user interface, for example, to allow a user to grasp, manipulate, move, etc. the guidewire sheath drive component 140 to thereby move the guidewire sheath 130 relative to one or more other portions of the catheter 100.

The clot treatment component 150 can comprise one or more of the clot treatment components described in detail in U.S. Pat. Nos. 8,784,434; 10,342,571; and/or 10,912,577; the entireties of which are hereby incorporated by reference. In at least some embodiments, for example, the clot treatment component 150 can include one or more stents, baskets, disks, spheres, funnels, balloons, and/or tubes, individual ones of which can be a laser cut, braided, extruded, woven component, etc. The clot treatment component 150 can be positioned within the outer sheath lumen 114, for example, between the interior surface of the outer sheath 110 and the exterior surface of the guidewire sheath 130. Referring to FIG. 1B, which shows the clot treatment component 150 in a deployed or expanded configuration, the clot treatment component 150 can include a distal end portion 152*a* and a proximal end portion 152*b* opposite the distal end portion 152*a*. The clot treatment component 150 can be coupled to the catheter 100, e.g., at one or both of the end portions 152*a*, 152*b* and/or at one or more other suitable portions of the clot treatment component 150 between the end portions 152*a,b*. In at least some embodiments, for example, the distal end portion 152*a* of the clot treatment component 150 can be coupled to the guidewire sheath 130 (e.g., the distal tip 132*a*), and/or any other suitable sheath and/or component of the catheter 100. Additionally, or alternatively, the proximal end portion 152*b* of the clot treatment component 150 can be coupled to the guidewire sheath 130, and/or any other suitable sheath and/or component of the catheter 100. In embodiments where one end (e.g., the distal end portion 152*a*) of the clot treatment component 150 is coupled to the guidewire sheath 130, and/or another suitable sheath and/or component of the catheter 100, the other end (e.g., the proximal end portion 152*b*) of the clot treatment component 150 can move or slide relative to the catheter 100, for example, along the exterior surface of the guidewire sheath 130 and/or at least partially between the distal end portion 112*a* of the outer sheath 110 and a proximal end portion 138 of the distal tip 132*a*. In at least some embodiments, the clot treatment component 150 is not coupled to the catheter 100 (e.g., free floating) and both the distal end portion 152*a* and the proximal end portion 152*b* can move or slide relative to each other and/or the catheter 100, e.g., while being retained on the guidewire sheath 130 via mechanical interference with the proximal end portion 138 of the distal tip 132*a* and/or the distal end portion 112*a* of the outer sheath 110. In these and other embodiments, the clot treatment component 150 can be configured to deploy/expand (e.g., radially deployed/expanded, longitudinally deployed/expanded, and the like) when the catheter 100 transitions from the first configuration 101*a* (FIG. 1A) to the second configuration 101*b* (FIG. 1B). The clot treatment component 150 can expand automatically, for example, in response to movement (e.g., by the user) of one or more of the sheaths and/or other components of the catheter 100.

Referring to FIGS. 1A, 1B, 6A, and 6B together, during a clot treatment procedure, the catheter 100 can be transitioned between the first configuration 101*a* (FIG. 1A) and the second configuration 101*b* (FIG. 1B) by moving one or more of the catheter's components and/or sheaths. As shown in the embodiment illustrated in FIG. 1B, for example, the outer sheath drive component 120 has been moved proximally relative to the guidewire sheath 130 to move the outer sheath 110 in the proximal direction and/or away from the distal terminus 136. This transitions the catheter 100 from the first configuration 101*a* to and/or at least partially toward the second configuration 101*b*. As the outer sheath 110 moves proximally, the clot treatment component 150 is progressively exposed in a distal-to-proximal motion that allows the clot treatment component 150 to deploy/expand from the first (e.g., delivery) state (FIG. 1A) to and/or at least partially toward the second (e.g., deployed) state (FIG. 1B). In the embodiment illustrated in FIG. 1A, for example, the clot treatment component 150 is positioned completely within the outer sheath lumen 114, between the interior surface of the outer sheath 110 and the exterior surface of the guidewire sheath 130, such that the outer sheath 110 restricts expansion (e.g., radial expansion, longitudinal expansion, etc.) of the clot treatment component 150. Accordingly, moving the outer sheath 110 in the proximal direction removes the constraint around the clot treatment component 150 such that it can expand (e.g., automatically expand) from the first state (FIG. 1A) to and/or at least partially toward the second state (FIG. 1B). The clot treatment component 150 may be configured to expand automatically due to material properties such as memory (e.g., shape memory), mechanically in response to application of a tensile or compressive force, via a balloon, and/or another suitable configuration. With the clot treatment component 150 in the second state and/or the catheter 100 in the second configuration 101*b*, the catheter 100 can be used to treat/remove clot material within a patient.

The catheter 100 can be returned from the second configuration 101*b* to the first configuration 101*a* by moving the outer sheath 110 in the distal direction and/or toward the distal terminus 136, for example, by moving the outer sheath drive component 120 in the distal direction. The clot treatment component 150 can be configured to return to the first state (FIG. 1A) as the catheter 100 is transitioned from the second configuration 101*b* toward the first configuration 101*a*. In at least some embodiments, for example, the proximal end portion 152*b* of the clot treatment component 150 can be radially sloped or tapered such that, as the outer sheath 110 is moved distally, the proximal end portion 152*b* can be received within the outer sheath lumen 114 and continued distal movement of the outer sheath 110 can collapse, enclose, and/or otherwise sheath the clot treatment component 150 (e.g., within the outer sheath 110). Additionally, or alternatively, the clot treatment component 150 can be sheathed by applying a tensile or compressive force to the clot treatment component 150, such as by moving the guidewire sheath 130 relative to the outer sheath 110 when the clot treatment component 150 is coupled to one or both of these sheaths 110, 130.

Additionally, or alternatively, the catheter 100 can be transitioned between the first and second configurations 101*a*, 101*b* by moving the guidewire sheath 130 relative to the outer sheath 110. In at least some embodiments, for example, the guidewire sheath drive component 140 can be moved distally relative to the outer sheath 110 to move the guidewire sheath 130 in the distal direction and/or outwardly from within the distal end portion 112*a* of the outer sheath 110. This can transition the catheter 100 from the first configuration 101*a* to and/or at least partially toward the second configuration 101*b*. As the guidewire sheath 130 moves distally, the clot treatment component 150 can be removed from within the outer sheath lumen 114 to expand/deploy, as described above. The catheter 100 can also be transitioned from the second configuration 101*b* to the first configuration 101*a* by moving the guidewire sheath drive component 140 in the proximal direction to move the guidewire sheath 130 proximally. This can reposition the clot treatment component 150 within the outer sheath lumen 114, as described above. In these and other embodiments, the catheter 100 can be transitioned between the first and second configurations 101*a*, 101*b* by moving the outer sheath drive component 120 and the guidewire sheath drive component 140 in combination, for example, sequentially and/or concurrently.

Figure 2A:
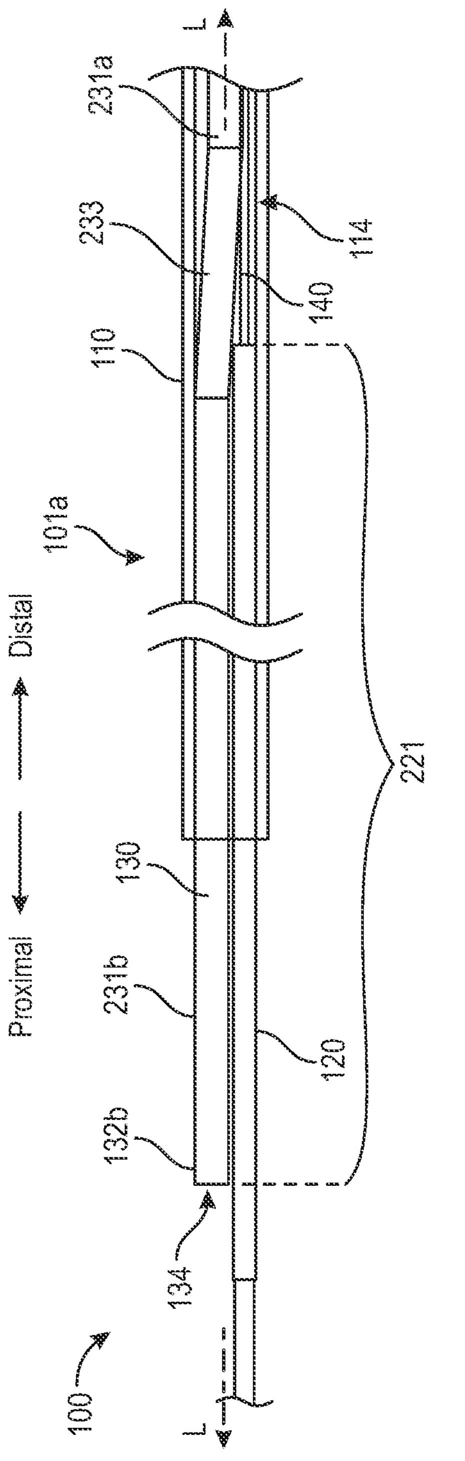
FIGS. 2A and 2B are enlarged side views of a portion of the clot treatment catheter of FIGS. 1A and 1B in the first and second configurations, respectively, in accordance with embodiments of the present technology.
Figure 2B:
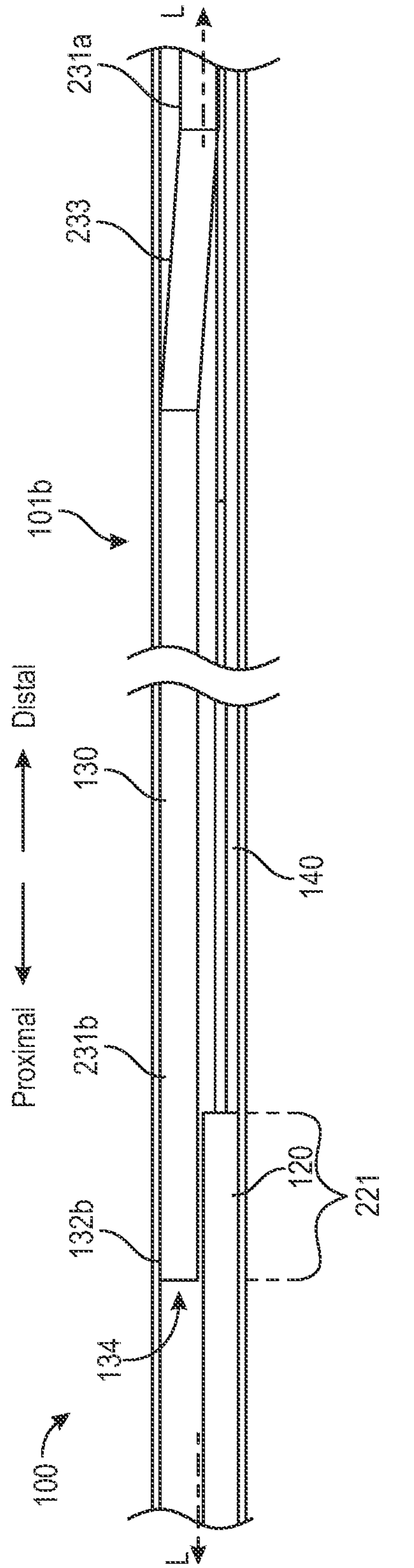

FIGS. 2A and 2B are enlarged side views of a portion of the catheter 100 of FIGS. 1A and 1B in the first configuration 101*a* and the second configuration 101*b*, respectively, in accordance with embodiments of the present technology. In FIGS. 2A and 2B, aspects of the catheter 100 are illustrated as transparent for clarity. The guidewire sheath 130 can include a distal segment 231*a*, a proximal segment 231*b* opposite the distal segment 231*a*, and a third segment 233 (which can also be referred to as an "intermediate segment," a "medial segment," a "transition segment," a "bridging segment," and the like) extending between the distal segment 231*a* and the proximal segment 231*b*. The distal segment 231*a* can be generally or substantially aligned/coincident with a longitudinal axis L of the catheter 100, such that the distal segment 231*a* can be generally or substantially concentric with the catheter 100 and/or centered within the outer sheath lumen 114. The proximal segment 231*b* can be offset with respect to the axis of the distal segment 231*a*, and the third segment 233 can be an angled intermediate segment that provides a sufficiently smooth transition between the distal segment 231*a* and the proximal segment 231*b* for tracking along a guidewire (not shown). The clot treatment component 150 (FIGS. 1A and 1B) can be coupled to the distal segment 231*a*, such that the clot treatment component 150 can be centered within the outer sheath lumen 114. In some aspects of the present technology, centering the clot treatment component 150 within the outer sheath lumen 114 is expected to improve an operator's ability to repeatedly and/or consistently unsheathe and re-sheathe the clot treatment component 150 (e.g., out from or back within the outer sheath 110) during a clot treatment procedure, as described in detail above with reference to FIGS. 1A and 1B.

The proximal segment 231*b* can be generally or substantially parallel to the longitudinal axis L. In at least some embodiments, for example, the proximal segment 231*b* is not concentric/colinear with the longitudinal axis L and/or the distal segment 231*a*, as shown in FIGS. 2A and 2B. The outer sheath drive component 120 can be generally or substantially parallel to the proximal segment 231*b* and/or on an opposite side of the longitudinal axis L from the proximal segment 231*b*. Although the outer sheath drive component 120 and the guidewire sheath 130 are shown spaced apart in the embodiment illustrated in FIGS. 2A and 2B for illustrative clarity, it will be appreciated that, in practice, the outer sheath drive component 120 may or may not contact the guidewire sheath 130. The outer sheath drive component 120 can be sized such that a region 221 of the outer sheath drive component 120 maintains an overlapping alignment with at least part of the guidewire sheath lumen 134. Accordingly, the outer sheath drive component 120 can be at least partially coextensive, conterminous, and/or otherwise positioned alongside with the guidewire sheath lumen 134 when the catheter 100 is in the first and second configurations 101*a*, 101*b*. In some embodiments, for example, the region 221 can be coextensive and/or conterminous with at least part of the proximal segment 231*b* when the catheter 100 is in the first and second configurations 101*a*, 101*b* (FIGS. 1A and 1B, respectively). In some aspects of the present technology, the coextensive and/or conterminous alignment between the outer sheath drive component 120 and the guidewire sheath 130 is expected to improve the user's ability to repeatedly and/or consistently unsheathe and re-sheathe the clot treatment component 150 during a clot treatment procedure while also maintaining an open lumen through the catheter 100 (e.g., the guidewire sheath lumen 134). For example, the coextensive and/or conterminous relationship between the proximal segment 231*b* of the guidewire sheath 130 and the region 221 of the outer sheath drive component 120 in the second configuration 101*b* can maintain the guidewire sheath 130 and the outer sheath drive component 120 in a slidable relationship relative to each other and allow the guidewire sheath 130 to be moved proximally to return the catheter 100 to the first configuration 101*a*. The relatively short length of the guidewire sheath 130 is expected to allow the user to reload the guidewire and/or insert other devices along the guidewire during the clot treatment procedure. In other embodiments, the region 221 of the outer sheath drive component 120 may not be in overlapping alignment with at least part of the guidewire sheath lumen 134 when the catheter 100 is in the first and second configurations 101*a*, 101*b*, but can still maintain advantages described above.

The intermediate segment 233 can be angled or sloped relative to the longitudinal axis L as described above. For example, the intermediate segment 233 can be angled radially inward, for example, toward the longitudinal axis L from the proximal segment 231*b* toward the distal segment 231*a* and/or toward the guidewire sheath drive component 140. The intermediate segment 233 can connect the distal and proximal segments 231*a*, 231*b*, such that the guidewire sheath lumen 134 and/or a guidewire (not shown) can extend fully through the guidewire sheath 130 as described above. Additionally, or alternatively, the guidewire sheath drive component 140 can be operably coupled to the guidewire sheath 130 at or near the intermediate segment 233.

Figure 3A:
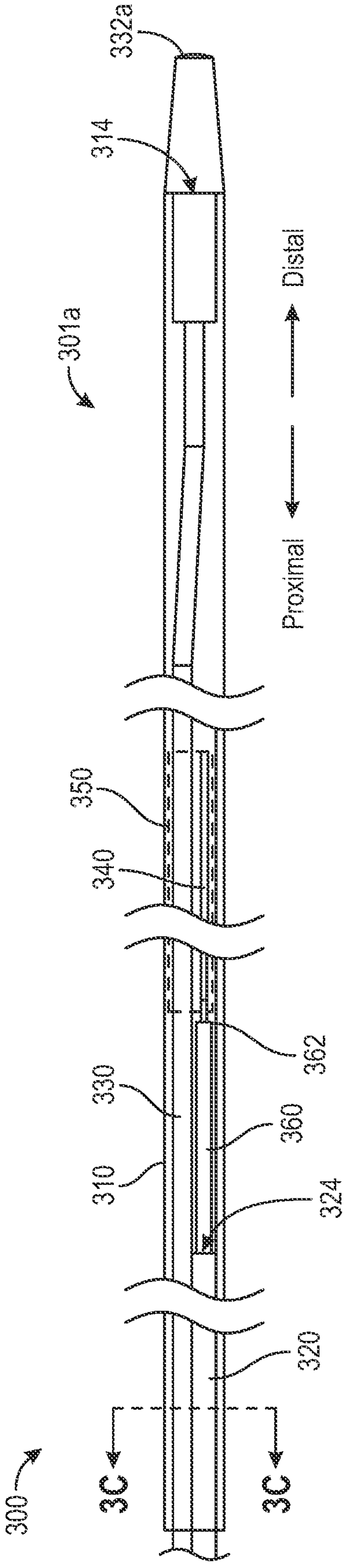
FIGS. 3A and 3B are side views of another clot treatment catheter in a first configuration and a second configuration, respectively, in accordance with embodiments of the present technology.
Figure 3B:
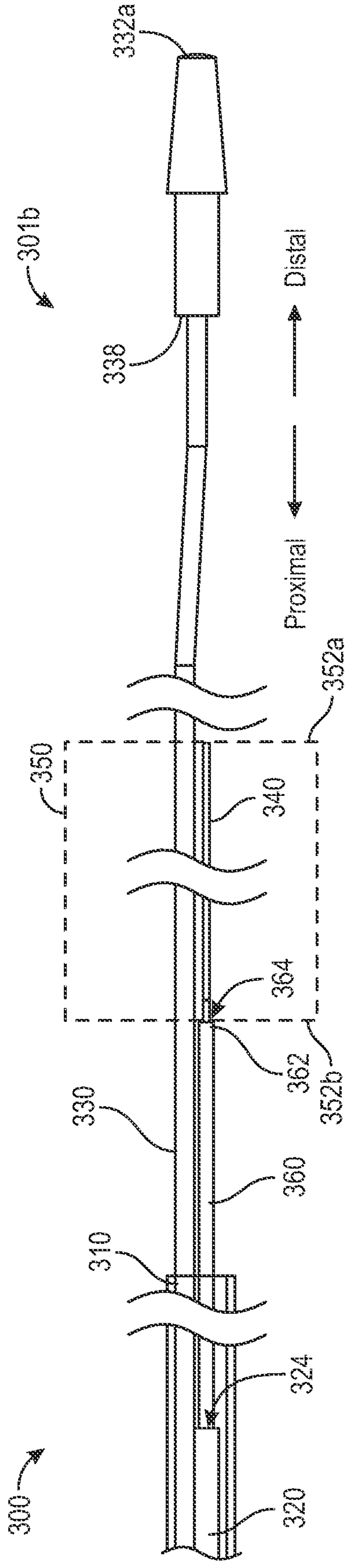
Figure 3C:
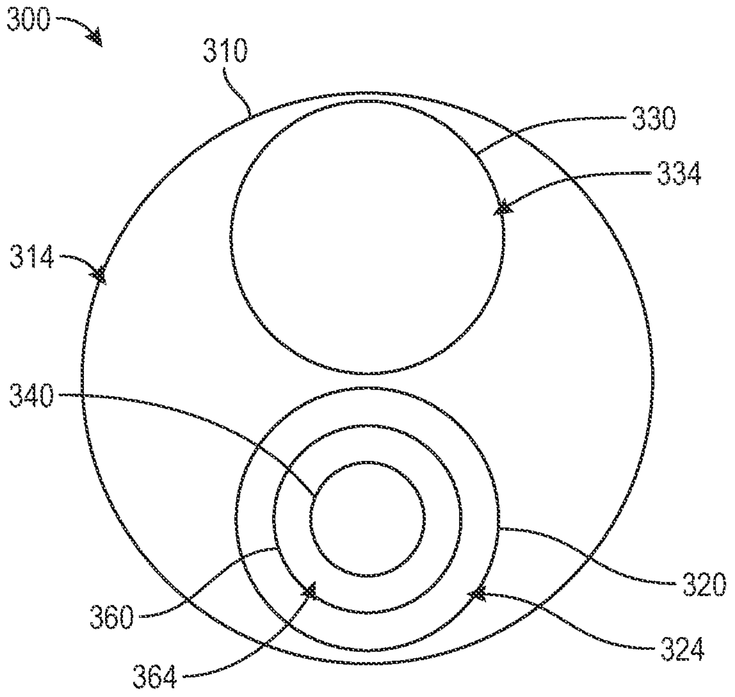
FIG. 3C is a partially-schematic cross-sectional view of the clot treatment catheter of FIGS. 3A and 3B taken along line 3C-3C of FIG. 3A in accordance with embodiments of the present technology.

FIGS. 3A and 3B are side views of another clot treatment and/or clot removal catheter 300 ("catheter 300") in a first configuration 301*a* and a second configuration 301*b*, respectively, in accordance with embodiments of the present technology. In FIGS. 3A and 3B, aspects of the catheter 300 are illustrated as transparent for clarity. FIG. 3C is a partially-schematic cross-sectional view of the catheter 300 taken along line 3C-3C of FIG. 3A. The catheter 300 can include some aspects that are generally similar or identical in structure and/or function to aspects of the catheter 100 of FIGS. 1A-2B, with like reference numbers (e.g., outer sheath 310 versus the outer sheath 110 of FIGS. 1A-2B) indicating generally similar or identical aspects. Additionally, in the illustrated embodiment, the catheter 300 includes a clot treatment drive component 360. The clot treatment drive component 360 can be positioned (e.g., radially, telescopically, and the like) between the outer sheath drive component 320 and the guidewire sheath drive component 340, such that each of the outer sheath drive component 320, the guidewire sheath drive component 340, and the clot treatment drive component 360 can be moved independently in the proximal direction and/or distal direction. In the illustrated embodiment, for example, the guidewire sheath drive component 340 is slidably disposed within the clot treatment drive component lumen 364 (FIG. 3B) and the clot treatment drive component 360 is slidably disposed within the outer sheath drive component lumen 324.

The clot treatment drive component 360 can include an elongated tube or member having a distal end portion 362 and a lumen 364 ("clot treatment drive component lumen 364"). The clot treatment drive component 360 can be operably coupled to a clot treatment component 350 (shown schematically in FIGS. 3A and 3B). In at least some embodiments, for example, the distal end portion 362 of the clot treatment drive component 360 can be coupled to a proximal end portion 352*b* of the clot treatment component 350, such as shown in FIG. 3B. In these and other embodiments, any other suitable portion or end of the clot treatment drive component 360 can be coupled to any other suitable portion or end of the clot treatment component 350. Additionally, or alternatively, any other suitable portion or end of the clot treatment component 350 (e.g., distal end portion 352*a*) can be coupled to the guidewire sheath 330 and/or a proximal end portion 338 of a distal tip 332*a* of the guidewire sheath 330.

During a clot treatment procedure, the outer sheath drive component 320 and/or the guidewire sheath drive component 340 can be moved to transition the catheter 300 between the first configuration 301*a* and the second configuration 301*b*, such as described in detail above with reference to FIGS. 1A-2B. Additionally, the clot treatment drive component 360 and/or guidewire sheath drive component 340 can be moved to transition the clot treatment component 350 between the first state (FIG. 3A) and the second state (FIG. 3B). In at least some embodiments, for example, the clot treatment drive component 360 can be moved distally to expand/deploy the clot treatment component 350 from the first (e.g., delivery) state to and/or at least partially toward the second (e.g., deployed) state. In other embodiments, the clot treatment drive component 360 can be moved proximally to expand/deploy the clot treatment component 350 from the first state to and/or at least partially toward the second state. Additionally, or alternatively, the clot treatment drive component 360 can be moved distally to return the clot treatment component 350 the second state to and/or at least partially toward the first state, for example, to position/sheathe the clot treatment component 350 within the outer sheath lumen 314, as shown in FIG. 3A. In other embodiments, the clot treatment drive component 360 can be moved proximally to return the clot treatment component 350 the second state to and/or at least partially toward the first state. In these and other embodiments, the clot treatment component 350 can automatically transition between the first and second states, such as described in detail above regarding FIGS. 1A and 1B. In at least some embodiments, for example, the clot treatment component 350 can be biased toward one state (e.g., the second state), and the clot treatment drive component 360 and/or guidewire sheath drive component 340 can be moved to control the degree and/or rate that the clot treatment component 350 transitions toward the biased state. In these and other embodiments, the clot treatment drive component 360 and/or guidewire sheath drive component 340 can be moved to adjust (e.g., increase and/or decrease) one or more dimensions (e.g., length, width, diameter, cross-sectional area, and the like) and/or adjust one or more characteristics/mechanical properties (e.g., radial force, tension, compression, shape, and the like) of the clot treatment component 350. For example, moving the clot treatment drive component 360 distally to expand/deploy the clot treatment component 350, as described above, may also cause a length of the clot treatment component 350 to decrease and/or a cross-sectional area of the clot treatment component 350 to increase.

Although the catheter 300 includes one clot treatment drive component 360 in the embodiment illustrated in FIGS. 3A-3C, in other embodiments the catheter 300 can include more clot treatment drive components, such as at least two, three, four, five, or any other suitable number of clot treatment drive components. Each additional clot treatment drive component can be positioned between (e.g., radially between, telescopically, and the like) the outer sheath drive component 320 and the guidewire sheath drive component 340, at least generally similar to the position of the clot treatment drive component 360. For example, a second clot treatment drive component (not shown in FIGS. 3A-3C) can be slidably disposed within the clot treatment drive component lumen 364, between an interior surface of the clot treatment drive component 360 and an exterior surface of the guidewire sheath drive component 340. Each additional clot treatment drive component can be operably coupled to a respective portion or end of the clot treatment component 350, such that each additional clot treatment drive component can increase the user's ability to adjust/control the clot treatment component 350. In at least some embodiments, for example, each additional clot treatment drive component can be configured to adjust at least one dimension of the clot treatment component 350.

Figure 4A:
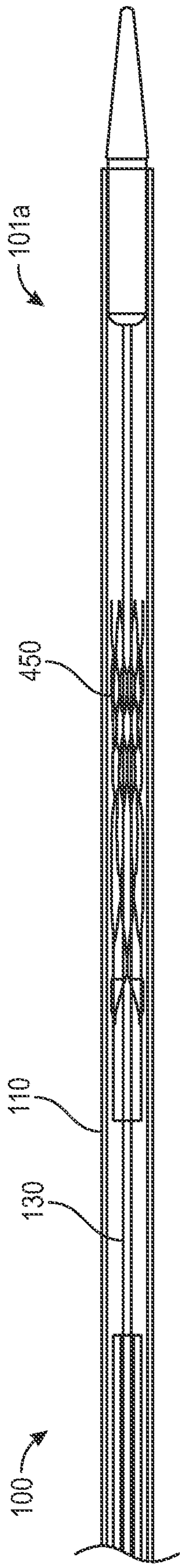
FIGS. 4A and 4B are side views of the clot treatment catheter of FIGS. 1A-1C in a first configuration and a second configuration, respectively, in accordance with embodiments of the present technology.
Figure 4B:
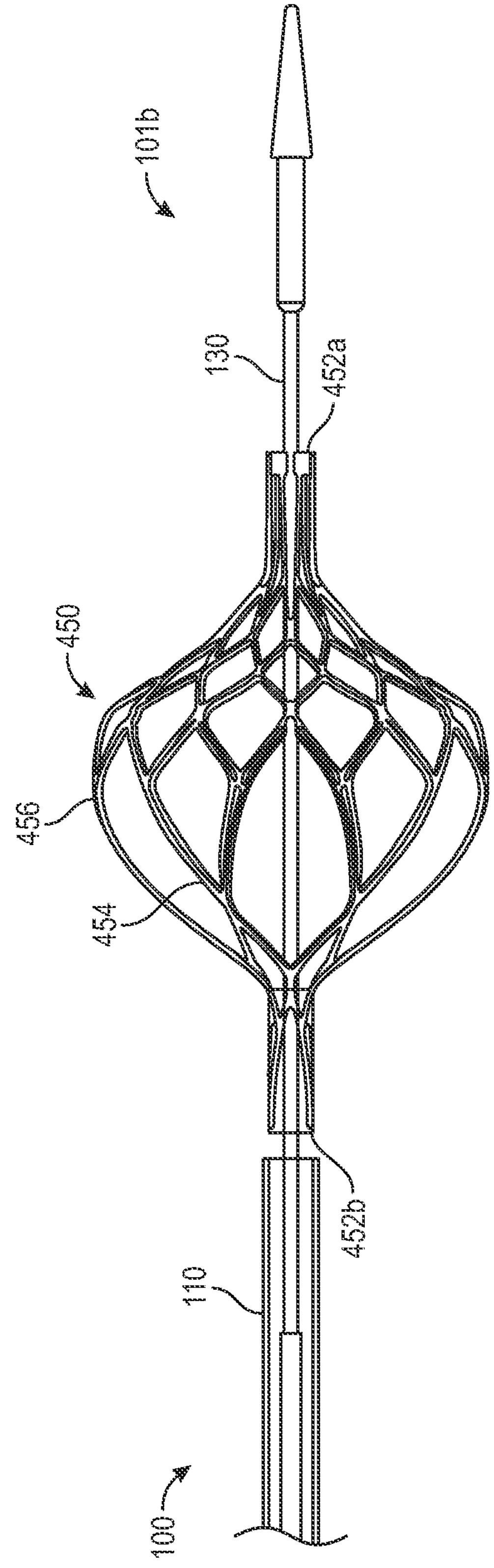

FIGS. 4A and 4B are side views of the clot treatment catheter 100 in the first configuration 101*a* and the second configuration 101*b*, respectively, in accordance with embodiments of the present technology. In FIGS. 4A and 4B, aspects of the catheter 100 are illustrated as transparent for clarity. In the illustrated embodiment, the catheter 100 includes a clot treatment component 450 having a plurality of struts 454. Individual ones of the struts 454 can extend at least partially between the distal end portion 452*a* and the proximal end portion 452*b* of the clot treatment component 450. In the illustrated embodiment, the proximal end portion 452*b* is coupled to (e.g., configured to move with) the guidewire sheath 130 and the distal end portion 452*a* is configured to move/slide along the guidewire sheath 130. When the catheter 100 is in the second configuration 101*b*, the clot treatment component 450 can be expanded/deployed radially outward from the guidewire sheath 130. In some embodiments, for example, the struts 454 can be shape-memory struts and can automatically expand/deploy in response to movement of the guidewire sheath 130 and/or the outer sheath 110. The clot treatment component 450 can further include an apex or radially-extended portion 456 that defines a maximum outer dimension (e.g., width, radius, etc.) of the clot treatment component 405. When expanded/deployed, the clot treatment component 450 can be used to remove clot material from a within patient. Additional details regarding the clot treatment component can be found in U.S. Pat. Nos. 8,784,434, the entirety of which was previously incorporated by reference herein. Although the catheter 100 is carrying a single clot treatment component 450 in the embodiment shown in FIGS. 4A and 4B, in other embodiments, the catheter 100 can carrying multiple clot treatment components.

Figure 5:
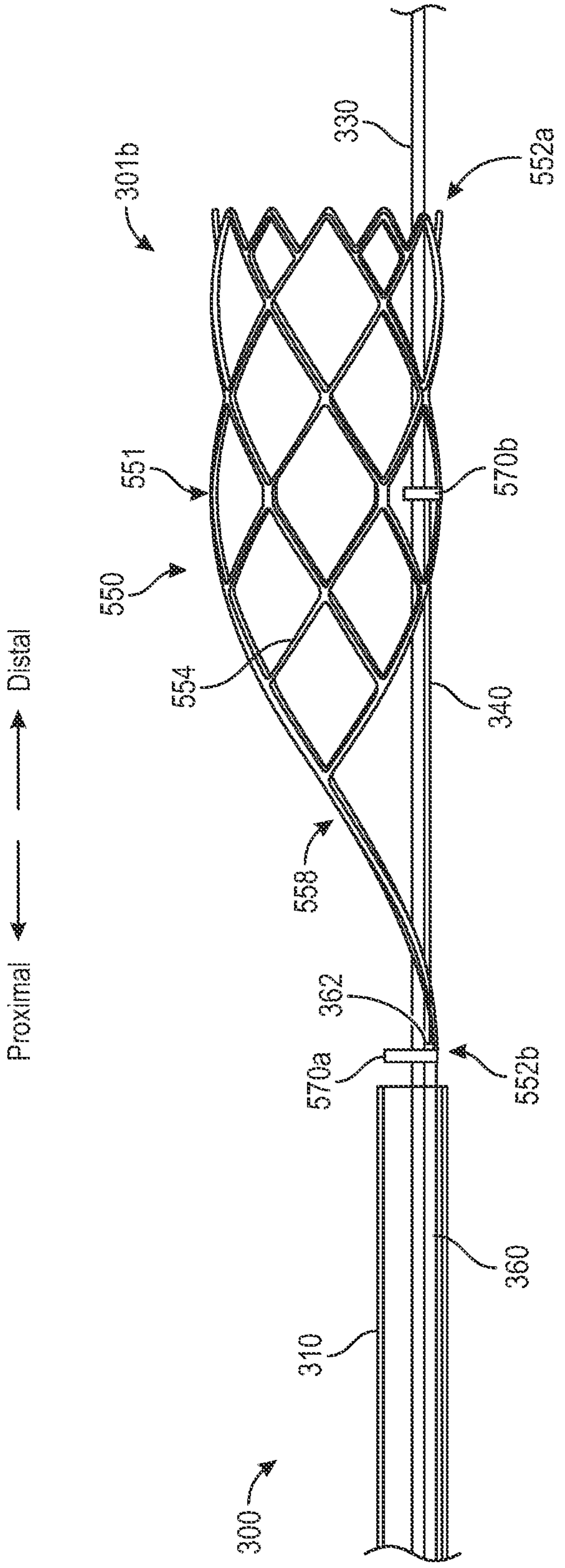
FIG. 5 is a side view of the clot treatment catheter of FIGS. 3A and 3B in the second configuration in accordance with embodiments of the present technology.

FIG. 5 is a side view of the clot treatment catheter 300 in the second configuration 301*b* in accordance with embodiments of the present technology. In FIG. 5, aspects of the catheter 300 are illustrated as transparent for clarity. In the illustrated embodiment, the catheter 300 includes a clot treatment component 550 including a coring element 551. The coring element 551 includes a cylindrical fenestrated structure defined by a plurality of struts 554. Individual ones of the struts 554 can extend at least partially between a distal end portion 552*a* and a proximal end portion 552*b* of the coring element 551. The coring element 551 can include a leading edge 558 at or near the proximal end portion 552*b* and configured to core or otherwise remove clot material from within a patient. For example, the coring element 551 can be expanded distal from clot material and retracted proximally such that the leading edge 558 engages the clot material to thereby capture and/or otherwise remove at least a portion of the clot material. In some embodiments, the clot treatment component 550 further includes an expandable bag or cylindrical portion coupled to the distal portion 552*a* of the coring element 551 and extending distally therefrom. The expandable bag can be a braided and/or mesh structure (e.g., a braided filament mesh structure) and can be configured to capture and retain the clot material after it is cored by the coring element 551. In some embodiments, a distal portion of the expandable bag can be coupled to the distal tip 332*a* (FIGS. 3A and 3B) of the guidewire sheath 330 such that movement of the guidewire sheath 330 relative to the coring element 551 can lengthen/shorten the expandable bag. Additional details regarding the clot treatment component 550 can be found in U.S. Pat. Nos. 10,342,571 and/or 10,912,577, the entireties of which were both previously incorporated by reference herein.

In the illustrated embodiment, the proximal end portion 552*b* of the coring element 551 is coupled to the clot treatment drive component 360. Specifically, the catheter 300 includes a first coupling component 570*a* configured to couple the proximal end portion 552*b* of the coring element 551 to the distal end portion 362 of the clot treatment drive component 360. With continued reference to the illustrated embodiment, the catheter 300 can include a second coupling component 570*b* configured to couple the coring element 551 to the guidewire sheath drive component 340 and/or the guidewire sheath 330. In other embodiments, the catheter 300 can include another clot treatment drive component (not shown in FIG. 5) coupled to the coring element 551 via the second coupling component 570*b*. In embodiments where the first and second coupling components 570*a-b* are both coupled to the coring element 551, the components/sheaths associated with the first and second coupling components 570*a-b* can be moved relative to each other to manipulate the coring element 551. For example, the distance between the first and second coupling components 570*a-b* can be decreased (e.g., by distally advancing the clot treatment drive component 360 and/or proximally retracting the guidewire sheath drive component 340 and/or the guidewire sheath 330) to cause the coring element 551 to shorten longitudinally and/or expand radially outward from the guidewire sheath 330. As another example, the distance between the first and second coupling components 570*a-b* can be increased (e.g., by proximally retracting the clot treatment drive component 360 and/or distally advancing the guidewire sheath drive component 340 and/or the guidewire sheath 330) to cause the coring element 551 to lengthen longitudinally and/or compress radially inwardly toward the guidewire sheath 330. In at least some embodiments, at least part of the clot treatment component 550 (e.g., the expandable bag described above) can be coupled to the distal tip 332*a* (FIGS. 3A and 3B) of the guidewire sheath 330 such that (i) moving the guidewire sheath 330 distally can lengthen the clot treatment component 550 longitudinally and/or compress the clot treatment component 550 radially inwardly toward the guidewire sheath 330 and (ii) moving the guidewire sheath 330 proximally can shorten the clot treatment component 550 longitudinally and/or expand the clot treatment component 550 radially outward away from the guidewire sheath 330, in addition to or in lieu of movement of one or more of the other sheaths/components of the catheter 300.

Figure 7:
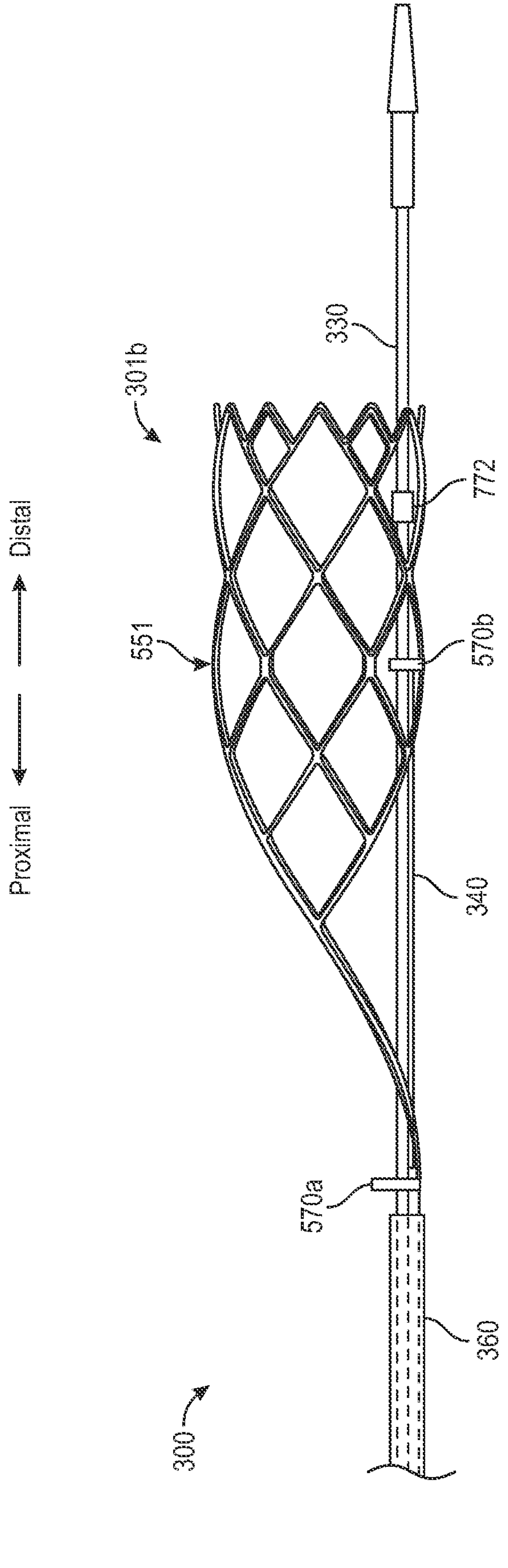
FIG. 7 is a side view of the clot treatment catheter of FIGS. 3A and 3B in the second configuration in accordance with embodiments of the present technology.

FIG. 7 is a side view of the clot treatment catheter 300 in the second configuration 301*b* in accordance with embodiments of the present technology. In FIG. 7, aspects of the catheter 300 are illustrated as transparent for clarity. In the illustrated embodiment, the catheter 300 includes the coring element 551 described previously with reference to FIG. 5. In the embodiment illustrated in FIG. 7, however, the second coupling component 570*b* is not coupled to the guidewire sheath drive component 340. Instead, the guidewire sheath drive component 340 is coupled to a drive cuff 772 (e.g., a stop member) positioned around the guidewire sheath 330 distally of the second coupling component 570*b*. The guidewire sheath drive component 340 can be slidably disposed through the second coupling component 570*b* such that the drive cuff 772 and/or the second coupling component 570*b* can be moved relative to one another. This relative movement of the drive cuff 772 and the second coupling component 570*b* can be used to change a configuration of the coring element 551 and/or the clot treatment component 550. For example, the drive cuff 772 can be moved proximally (e.g., by proximally retracting the guidewire sheath drive component 340 and/or the guidewire sheath 330) to contact the second coupling component 570*b* and cause the second coupling component 570*b* to move proximally. This, in turn, can decrease the distance between the first coupling component 570*a* and the second coupling component 570*b* and thereby cause the coring element 551 to shorten longitudinally and/or expand radially outward from the guidewire sheath 330. In some embodiments, the guidewire sheath drive component 340 can be biased in the proximal direction, such that the drive cuff 772 is biased proximally into engagement with the second coupling component 570*b* to cause the coring element 551 to shorten and/or expand radially outwardly from the guidewire sheath 330.

Figure 8:
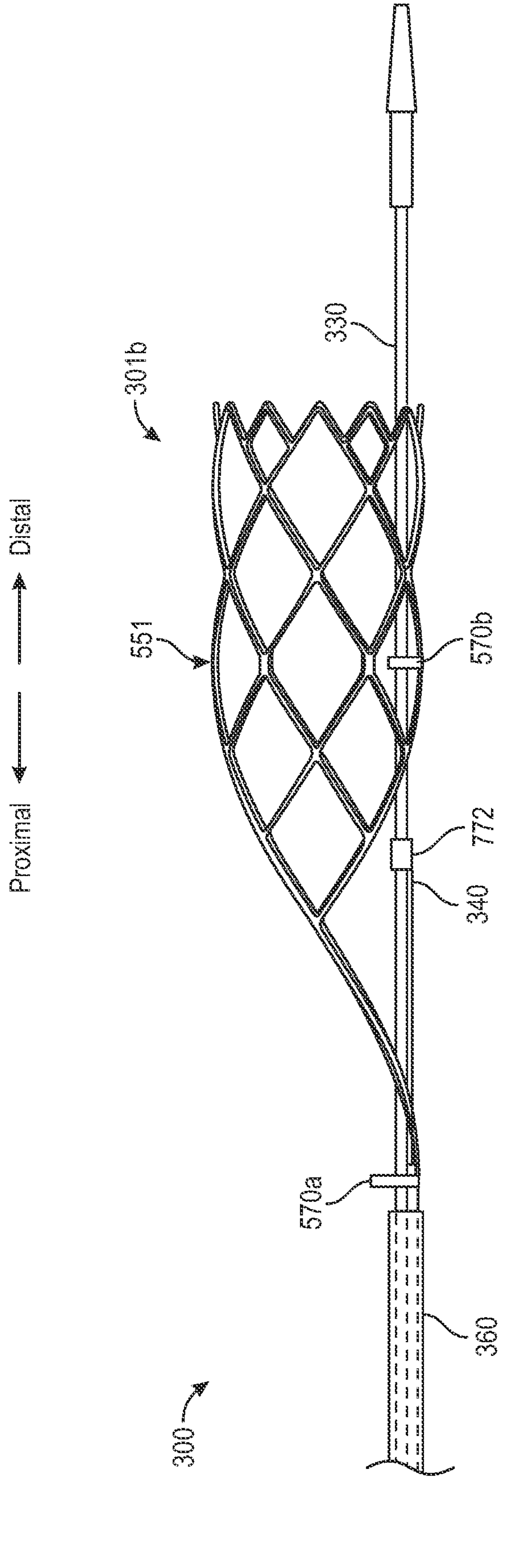
FIG. 8 side view of the clot treatment catheter of FIGS. 3A and 3B in the second configuration in accordance with embodiments of the present technology.

FIG. 8 is a side view of the clot treatment catheter 300 in the second configuration 301*b* in accordance with embodiments of the present technology. In FIG. 8, aspects of the catheter 300 are illustrated as transparent for clarity. The catheter 300 illustrated in FIG. 8 can include at least some features that are at least generally similar or identical in structure and/or function to the catheter 300 described previously with reference to FIG. 7. However, in the embodiment illustrated in FIG. 8, the drive cuff 772 is positioned around the guidewire sheath 330 proximally of the second coupling component 570*b*. Accordingly, the drive cuff 772 can be moved distally (e.g., by distally advancing the guidewire sheath drive component 340 and/or the clot treatment drive component 360) to contact the second coupling component 570*b* and increase the distance between the first coupling component 570*a* and the second coupling component 570*b* to cause the coring element 551 to lengthen longitudinally and/or compress radially inwardly toward the guidewire sheath 330. In some embodiments, the guidewire sheath drive component 340 can be biased in the distal direction, such that the drive cuff 772 is biased distally into engagement with the second coupling component 570*b* to cause the coring element 551 to lengthen and/or contract radially inwardly toward the guidewire sheath 330.

Accordingly, in some aspects of the present technology, a catheter can include an outer sheath, an outer sheath drive component operably coupled to the outer sheath, a guidewire sheath slidably disposed within the outer sheath, and a guidewire sheath drive component operably coupled to the guidewire sheath and slidably disposed within the outer sheath drive component. The outer sheath drive component can be moved proximally and/or distally to cause corresponding movement of the outer sheath. The guidewire sheath drive component can be moved proximally and/or distally to cause corresponding proximal and/or distal movement of the guidewire sheath. The movement of the outer sheath and/or the guidewire sheath can transition the catheter between a first configuration and a second configuration. In some embodiments, the catheter includes a clot treatment component carried within the outer sheath, and, during a procedure, the clot treatment component can be deployed from the outer sheath and/or repositioned within the outer sheath by moving one or both of the outer sheath drive component and the guide wire sheath drive component. For example, the clot treatment component can be carried within the outer sheath when the catheter is in the first configuration, and the clot treatment component can be deployed from the outer sheath when the catheter is in the second configuration. In these and other embodiments, the catheter can include at least one clot treatment drive component operably coupled to the clot treatment component. The clot treatment drive component can be positioned between (e.g., radially between, telescopically between, and the like) the outer sheath drive component and the guidewire sheath drive component. During a procedure, the clot treatment drive component can be moved proximally and/or distally to deploy, sheath, and/or change at least one dimension (e.g., length, width, diameter, cross-sectional area, and the like) of the clot treatment component.

Several aspects of the present technology are set forth in the following examples:

1. An intravascular catheter for treatment of clot material from within a blood vessel of a human patient, comprising:

an outer sheath having an outer sheath lumen;

an outer sheath drive component having an outer sheath drive component lumen, wherein the outer sheath drive component is operably coupled to the outer sheath;

a guidewire sheath including a guidewire sheath lumen configured to receive a guidewire, wherein at least a portion of the guidewire sheath is slidably disposed within the outer sheath lumen;

a guidewire sheath drive component slidably disposed within the outer sheath drive component lumen, wherein the guidewire sheath drive component is operably coupled to the guidewire sheath; and a clot treatment component coupled to the guidewire sheath, wherein the clot treatment component is configured to transition between (i) a first configuration in which the clot treatment component is positioned within the outer sheath lumen, and (ii) a second configuration in which at least a portion of the clot treatment component is exposed from the outer sheath lumen in response to movement of the outer sheath drive component, the guidewire sheath drive component, or both the outer sheath drive component and the guidewire sheath drive component.

2. The catheter of example 1, further comprising a clot treatment drive component slidably disposed within the outer sheath drive component lumen and operably coupled to the clot treatment component, wherein the clot treatment component is configured to transition between the first configuration and the second configuration in response to movement of the clot treatment drive component, the outer sheath drive component, the guidewire sheath drive component, or any two or more of the outer sheath drive component, the guidewire sheath drive component, and clot treatment drive component.

3. The catheter of example 1 or example 2 wherein the outer sheath drive component includes a region configured to overlap with a portion of the guidewire sheath when the clot treatment component is in the first configuration and the second configuration.

4. The catheter of example 3 wherein the guidewire sheath includes a proximal segment and a distal segment, wherein at least part of the proximal segment is configured to be conterminous with the portion of the outer sheath drive component, and wherein the distal segment is centered within the outer sheath lumen.

5. The catheter of example 4 wherein at least a portion of the clot treatment component is coupled to the distal segment of the guidewire sheath.

6 The catheter of example 5 wherein the distal segment of the guidewire sheath includes a distal tip of the catheter, and wherein at least the portion of the clot treatment component is coupled to the distal tip.

7. The catheter of any of examples 4-6 wherein at least a portion the clot treatment component is slidably disposed on the distal segment.

8. The catheter of any of examples 4-7 wherein the guidewire sheath further includes an intermediate segment extending between the distal segment and the proximal segment, wherein the intermediate segment is sloped radially inward from the proximal segment toward the distal segment.

9. The catheter of example 1 wherein the guidewire sheath includes a distal segment centered within the outer sheath lumen, and wherein at least a portion of the clot treatment component is coupled to the distal segment of the guidewire sheath.

10. The catheter of example 9 wherein the distal segment of the guidewire sheath includes a distal tip of the catheter, and wherein at least the portion of the clot treatment component is coupled to the distal tip.

11. The catheter of example 9 or example 10 wherein at least a portion the clot treatment component is slidably disposed on the distal segment of the guidewire sheath.

12. The catheter of any of examples 9-11 wherein the guidewire sheath further includes a proximal segment positioned radially outwardly from the distal segment of the guidewire sheath.

13. The catheter of example 12 wherein the proximal segment is not centered within the outer sheath lumen.

14. The catheter of example 12 or example 13 wherein the guidewire sheath further includes an intermediate segment extending between the distal segment and the proximal segment, wherein the intermediate segment is sloped radially inward from the proximal segment toward the distal segment.

15. A method for intravascular treatment of clot material from within a blood vessel of a human patient, the method comprising:

advancing a catheter distally through the blood vessel; and transitioning the catheter from (i) a first configuration in which a clot treatment component of the catheter is positioned within an outer sheath lumen of an outer sheath of the catheter, and (ii) a second configuration in which at least a portion of the clot treatment component is exposed from the outer sheath lumen, wherein the catheter includes (a) an outer sheath drive component including an outer sheath drive component lumen and coupled to the outer sheath and (b) an elongate member operably coupled to the clot treatment component and slidably disposed within the outer sheath drive component lumen, and wherein transitioning the catheter includes at least one of— moving the outer sheath drive component in a first direction relative to the clot treatment component to cause the outer sheath to uncover at least the portion of the clot treatment component, and/or moving the elongate member in a second direction relative to the outer sheath to cause at least the portion of the clot treatment component to extend beyond the outer sheath lumen.

16. The method of example 15 wherein the second direction is opposite the first direction.

17. The method of example 15, further comprising causing the clot treatment component to expand when the catheter is in the second configuration.

18. The method of example 17 wherein causing the clot treatment component to expand includes transitioning the catheter to the second configuration to allow the clot treatment component to expand.

19. The method of example 17 wherein causing the clot treatment component to expand includes moving a clot treatment drive component operably coupled to the clot treatment component relative to a guidewire sheath positioned within the catheter and adjacent to the outer sheath drive component.

20 The method of example 17 wherein causing the clot treatment component to expand includes moving a drive cuff of the catheter to cause the expansion of the clot treatment component.

21 The method of example 20 wherein moving the drive cuff includes moving the drive cuff in the first direction relative to the clot treatment component to drive the expansion of the clot treatment component.

22 The method of example 20 wherein moving the drive cuff includes moving the drive cuff in the first direction relative to the clot treatment component to allow the clot treatment component to expand.

23 The method of any of examples 15-22, wherein the elongate member includes a guidewire sheath drive component, and wherein moving the elongate member includes moving the guidewire sheath drive component in the second direction relative to the outer sheath to cause at least the portion of the clot treatment component to extend beyond the outer sheath lumen.

24. The method of example 23 wherein moving the guidewire sheath drive component includes causing movement of a guidewire sheath operably coupled to the guidewire sheath drive component, and wherein the clot treatment component is operably coupled to the guidewire sheath so that causing movement of the guidewire sheath includes causing at least the portion of the clot treatment component to extend beyond the outer sheath lumen.

25. A catheter for treating a human patient, the catheter comprising:

an outer sheath having an outer sheath lumen;

an outer sheath drive component having an outer sheath drive component lumen, wherein the outer sheath drive component is slidably disposed within the outer sheath lumen and operably coupled to the outer sheath;

a guidewire sheath including a guidewire sheath lumen configured to receive a guidewire, wherein at least a portion of the guidewire sheath is slidably disposed within the outer sheath and laterally adjacent to the outer sheath drive component; and a guidewire sheath drive component slidably disposed within the outer sheath drive component, wherein the guidewire sheath drive component is operably coupled to the guidewire sheath;

a clot treatment component coupled to the guidewire sheath; and a clot treatment drive component slidably disposed within the outer sheath drive component lumen and operably coupled to the clot treatment component, wherein— the catheter is configured to transition between a (i) first configuration in which the clot treatment component is positioned within the outer sheath lumen, and (ii) a second configuration in which at least a portion of the clot treatment component is exposed from the outer sheath lumen in response to movement in response to at least one of (a) first movement the outer sheath drive component relative to the guidewire sheath in a first direction, and (b) second movement of the guidewire sheath drive component relative to the outer sheath in a second direction, and the clot treatment drive component is configured to transition the clot treatment component between (i) a first state in which the clot treatment component has a first dimension, and (ii) a second state in which the clot treatment component has a second dimension greater or less than the first dimension.

26. The catheter of example 25 wherein:

in the first state, the clot treatment component has a first mechanical property, and in the second state, the clot treatment component has a second mechanical property.

27. The catheter of example 26 wherein:

the first mechanical property includes at least one of a first radial force, a first tensile force, a first compressive force, and/or a first shape, and the second mechanical property includes at least one of a second radial force, a second tensile force, a second compressive force, and/or a second shape.

28 The catheter of any of examples 25-27 wherein the clot treatment component includes a mechanical thrombectomy component extending radially outwardly from the guidewire sheath.

29 The catheter of any of examples 25-27 wherein the clot treatment component includes a coring element having a proximally-facing leading edge.

30 The catheter of any of examples 25-29 wherein the clot treatment drive component is a first clot treatment drive component operably coupled to a first portion of the clot treatment component, the catheter further comprising a second clot treatment drive component slidably coupled to a second portion of the clot treatment component.

31. The catheter of example 30 wherein the first clot treatment drive component includes a first clot treatment drive component lumen, and wherein the second clot treatment drive component is slidably disposed within the first clot treatment drive component lumen.

32 The catheter of any of examples 25-31 wherein the second direction is opposite the first direction.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word “or” is expressly limited to mean only a single item exclusive from the other items in reference to a list of two or more items, then the use of “or” in such a list is to be interpreted as including (a) any single item in the list, (b) all of the items in the list, or (c) any combination of the items in the list. Additionally, the term “comprising” is used throughout to mean including at least the recited feature(s) such that any greater number of the same feature and/or additional types of other features are not precluded. It will also be appreciated that specific embodiments have been described herein for purposes of illustration but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. An intravascular catheter for treatment of clot material from within a blood vessel of a human patient, comprising:

an outer sheath having an outer sheath lumen;

an outer sheath drive component having an outer sheath drive component lumen, wherein the outer sheath drive component is operably coupled to the outer sheath;

a guidewire sheath including a guidewire sheath lumen configured to receive a guidewire, wherein at least a portion of the guidewire sheath is slidably disposed within the outer sheath lumen;

a guidewire sheath drive component slidably disposed within the outer sheath drive component lumen, wherein the guidewire sheath drive component is operably coupled to the guidewire sheath; and a clot treatment component coupled to the guidewire sheath, wherein the clot treatment component is configured to transition between (i) a first configuration in which the clot treatment component is positioned within the outer sheath lumen, and (ii) a second configuration in which at least a portion of the clot treatment component is exposed from the outer sheath lumen in response to movement of the outer sheath drive component, the guidewire sheath drive component, or both the outer sheath drive component and the guidewire sheath drive component.

2. The catheter of claim 1, further comprising a clot treatment drive component slidably disposed within the outer sheath drive component lumen and operably coupled to the clot treatment component, wherein the clot treatment component is configured to transition between the first configuration and the second configuration in response to movement of the clot treatment drive component, the outer sheath drive component, the guidewire sheath drive component, or any two or more of the outer sheath drive component, the guidewire sheath drive component, and clot treatment drive component.

3. The catheter of claim 1 wherein the outer sheath drive component includes a region configured to overlap with a portion of the guidewire sheath when the clot treatment component is in the first configuration and the second configuration.

4. The catheter of claim 3 wherein the guidewire sheath includes a proximal segment and a distal segment, wherein at least part of the proximal segment is configured to be conterminous with the portion of the outer sheath drive component, and wherein the distal segment is centered within the outer sheath lumen.

5. The catheter of claim 4 wherein at least a portion of the clot treatment component is coupled to the distal segment of the guidewire sheath.

6. The catheter of claim 5 wherein the distal segment of the guidewire sheath includes a distal tip of the catheter, and wherein at least the portion of the clot treatment component is coupled to the distal tip.

7. The catheter of claim 4 wherein at least a portion of the clot treatment component is slidably disposed on the distal segment.

8. The catheter of claim 4 wherein the guidewire sheath further includes an intermediate segment extending between the distal segment and the proximal segment, wherein the intermediate segment is sloped radially inward from the proximal segment toward the distal segment.

9. The catheter of claim 1 wherein the guidewire sheath includes a distal segment centered within the outer sheath lumen, and wherein at least a portion of the clot treatment component is coupled to the distal segment of the guidewire sheath.

10. The catheter of claim 9 wherein the distal segment of the guidewire sheath includes a distal tip of the catheter, and wherein at least the portion of the clot treatment component is coupled to the distal tip.

11. The catheter of claim 9 wherein at least a portion the clot treatment component is slidably disposed on the distal segment of the guidewire sheath.

12. The catheter of claim 9 wherein the guidewire sheath further includes a proximal segment positioned radially outwardly from the distal segment of the guidewire sheath.

13. The catheter of claim 12 wherein the proximal segment is not centered within the outer sheath lumen.

14. The catheter of claim 12 wherein the guidewire sheath further includes an intermediate segment extending between the distal segment and the proximal segment, wherein the intermediate segment is sloped radially inward from the proximal segment toward the distal segment.

15. A method for intravascular treatment of clot material from within a blood vessel of a human patient, the method comprising:

advancing a catheter distally through the blood vessel; and transitioning the catheter from (i) a first configuration in which a clot treatment component of the catheter is positioned within an outer sheath lumen of an outer sheath of the catheter, and (ii) a second configuration in which at least a portion of the clot treatment component is exposed from the outer sheath lumen, wherein the catheter includes (a) an outer sheath drive component including an outer sheath drive component lumen and coupled to the outer sheath and (b) an elongate member operably coupled to the clot treatment component and slidably disposed within the outer sheath drive component lumen, and wherein transitioning the catheter includes at least one of— moving the outer sheath drive component in a first direction relative to the clot treatment component to cause the outer sheath to uncover at least the portion of the clot treatment component, and/or moving the elongate member in a second direction relative to the outer sheath to cause at least the portion of the clot treatment component to extend beyond the outer sheath lumen.

16. The method of claim 15 wherein the second direction is opposite the first direction.

17. The method of claim 15, further comprising causing the clot treatment component to expand when the catheter is in the second configuration.

18. The method of claim 17 wherein causing the clot treatment component to expand includes transitioning the catheter to the second configuration to allow the clot treatment component to expand.

19. The method of claim 17 wherein causing the clot treatment component to expand includes moving a clot treatment drive component operably coupled to the clot treatment component relative to a guidewire sheath positioned within the catheter and adjacent to the outer sheath drive component.

20. The method of claim 17 wherein causing the clot treatment component to expand includes moving a drive cuff of the catheter to cause the expansion of the clot treatment component.

21. The method of claim 20 wherein moving the drive cuff includes moving the drive cuff in the first direction relative to the clot treatment component to drive the expansion of the clot treatment component.

22. The method of claim 20 wherein moving the drive cuff includes moving the drive cuff in the first direction relative to the clot treatment component to allow the clot treatment component to expand.

23. The method of claim 15, wherein the elongate member includes a guidewire sheath drive component, and wherein moving the elongate member includes moving the guidewire sheath drive component in the second direction relative to the outer sheath to cause at least the portion of the clot treatment component to extend beyond the outer sheath lumen.

24. The method of claim 23 wherein moving the guidewire sheath drive component includes causing movement of a guidewire sheath operably coupled to the guidewire sheath drive component, and wherein the clot treatment component is operably coupled to the guidewire sheath so that causing movement of the guidewire sheath includes causing at least the portion of the clot treatment component to extend beyond the outer sheath lumen.

25. A catheter for treating a human patient, the catheter comprising:

an outer sheath having an outer sheath lumen;

an outer sheath drive component having an outer sheath drive component lumen, wherein the outer sheath drive component is slidably disposed within the outer sheath lumen and operably coupled to the outer sheath;

a guidewire sheath including a guidewire sheath lumen configured to receive a guidewire, wherein at least a portion of the guidewire sheath is slidably disposed within the outer sheath and laterally adjacent to the outer sheath drive component;

a guidewire sheath drive component slidably disposed within the outer sheath drive component, wherein the guidewire sheath drive component is operably coupled to the guidewire sheath;

a clot treatment component coupled to the guidewire sheath; and a clot treatment drive component slidably disposed within the outer sheath drive component lumen and operably coupled to the clot treatment component, wherein— the catheter is configured to transition between a (i) first configuration in which the clot treatment component is positioned within the outer sheath lumen, and (ii) a second configuration in which at least a portion of the clot treatment component is exposed from the outer sheath lumen in response to movement in response to at least one of (a) first movement the outer sheath drive component relative to the guidewire sheath in a first direction, and (b) second movement of the guidewire sheath drive component relative to the outer sheath in a second direction, and the clot treatment drive component is configured to transition the clot treatment component between (i) a first state in which the clot treatment component has a first dimension, and (ii) a second state in which the clot treatment component has a second dimension greater or less than the first dimension.

26. The catheter of claim 25 wherein:

in the first state, the clot treatment component has a first mechanical property, and in the second state, the clot treatment component has a second mechanical property.

27. The catheter of claim 26 wherein:

the first mechanical property includes at least one of a first radial force, a first tensile force, a first compressive force, and/or a first shape, and the second mechanical property includes at least one of a second radial force, a second tensile force, a second compressive force, and/or a second shape.

28. The catheter of claim 25 wherein the clot treatment component includes a mechanical thrombectomy component extending radially outwardly from the guidewire sheath.

29. The catheter of claim 25 wherein the clot treatment component includes a coring element having a proximally-facing leading edge.

30. The catheter of claim 25 wherein the clot treatment drive component is a first clot treatment drive component operably coupled to a first portion of the clot treatment component, the catheter further comprising a second clot treatment drive component slidably coupled to a second portion of the clot treatment component.

31. The catheter of claim 30 wherein the first clot treatment drive component includes a first clot treatment drive component lumen, and wherein the second clot treatment drive component is slidably disposed within the first clot treatment drive component lumen.

32. The catheter of claim 25 wherein the second direction is opposite the first direction.

* * * * *